US011957699B2

(12) United States Patent
Namkung et al.

(10) Patent No.: US 11,957,699 B2
(45) Date of Patent: Apr. 16, 2024

(54) COMPOSITION COMPRISING PUNICALAGIN FOR INHIBITING PAR2 ACTIVITY

(71) Applicant: INDUSTRY-ACADEMIC COOPERATION FOUNDATION, YONSEI UNIVERSITY, Seoul (KR)

(72) Inventors: Wan Namkung, Incheon (KR); Sang Won Lee, Seoul (KR); Yo Han Seo, Jeollabuk-do (KR); Chin Hee Mun, Gyeonggi-do (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 430 days.

(21) Appl. No.: 17/264,959

(22) PCT Filed: Jul. 30, 2019

(86) PCT No.: PCT/KR2019/009457
§ 371 (c)(1),
(2) Date: May 7, 2021

(87) PCT Pub. No.: WO2020/027534
PCT Pub. Date: Feb. 6, 2020

(65) Prior Publication Data
US 2021/0308165 A1 Oct. 7, 2021

(30) Foreign Application Priority Data

Jul. 30, 2018 (KR) .................. 10-2018-0088883
Aug. 29, 2018 (KR) .................. 10-2018-0102307

(51) Int. Cl.
*A61K 31/7048* (2006.01)
*A61P 1/18* (2006.01)
*A61P 13/12* (2006.01)
*A61P 17/04* (2006.01)
*A61P 27/02* (2006.01)
*A61P 29/00* (2006.01)

(52) U.S. Cl.
CPC ............ *A61K 31/7048* (2013.01); *A61P 1/18* (2018.01); *A61P 13/12* (2018.01); *A61P 17/04* (2018.01); *A61P 27/02* (2018.01); *A61P 29/00* (2018.01)

(58) Field of Classification Search
None
See application file for complete search history.

(56) References Cited

U.S. PATENT DOCUMENTS

| 2006/0222671 | A1* | 10/2006 | Weidner | A61P 17/02 424/401 |
| 2007/0116841 | A1 | 5/2007 | Prakash et al. | |
| 2008/0214656 | A1* | 9/2008 | Lim | A61P 19/02 514/533 |
| 2010/0279951 | A1* | 11/2010 | Morgan | A61K 47/12 514/20.5 |

FOREIGN PATENT DOCUMENTS

KR      10-2006-0050555 A      5/2006

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Lin, C. C., Hsu, Y. F., Lin, T. C., Hsu, F. L., & Hsu, H. Y. (1998). Antioxidant and hepatoprotective activity of punicalagin and punicalin on carbon tetrachloride-induced liver damage in rats. Journal of Pharmacy and Pharmacology, 50(7), 789-794. (Year: 1998).*
Houston, D. M., Bugert, J., Denyer, S. P., & Heard, C. M. (2017). Anti-inflammatory activity of Punica granatum L.(Pomegranate) rind extracts applied topically to ex vivo skin. European Journal of Pharmaceutics and Biopharmaceutics, 112, 30-37. (Year: 2017).*
Hindi, N. (2013). Antimicrobial Activity of Different Aqueous Pomegranate (Rumman) Extracts against Different Human Pathogens. International Journal of Indigenous Medicinal Plants, 46, 2. (Year: 2013).*
Lee, C. J., Chen, L. G., Liang, W. L., & Wang, C. C. (2017). Multiple activities of Punica granatum Linne against acne vulgaris. International journal of molecular sciences, 18(1), 141. (Year: 2017).*
Xiaolong Xu et al., "Punicalagin Inhibits Inflammation in LPS-Induced RAW264.7 Macrophages via the Suppression of TLR4-Mediated MAPKs and NF-κB Activation", Inflammation, 2014, pp. 956-965, vol. 37, No. 3.
Tanmay A. Shah et al., "Evaluation of the effect of Punica granatum juice and punicalagin on NFκB modulation in inflammatory bowel disease", Mol Cell Biochem, 2016, pp. 65-74, 419(1-2).

(Continued)

*Primary Examiner* — Dale R Miller
(74) *Attorney, Agent, or Firm* — Sughrue Mion, PLLC

(57) ABSTRACT

The present invention relates to a composition for inhibiting PAR2 activity including punicalagin, and more specifically, the present invention provides a composition for inhibiting PAR2 activity including punicalagin, a stereoisomer thereof, or a pharmaceutically acceptable salt thereof, or a pharmaceutical composition, health functional food composition, or cosmetic composition for preventing or treating an inflammatory disease or pruritis.

3 Claims, 19 Drawing Sheets

(56) References Cited

OTHER PUBLICATIONS

Lamees A. Bensaad et al., "Anti-inflammatory potential of ellagic acid, gallic acid and punicalagin A&B isolated from Punica granatum", BMC Complementary and Alternative Medicine, 2017, pp. 1-10, vol. 17, No. 47.
Tonghui Ma et al., "Thiazolidinone CFTR inhibitor identified by high-throughput screening blocks cholera toxin-induced intestinal fluid secretion", The Journal of Clinical Investigation, 2002, pp. 1651-1658, vol. 110, No. 11.
Laura Garcia-Posadas et al., "A New Human Primary Epithelial Cell Culture Model to Study Conjunctival Inflammation", Investigative Ophthalmology & Visual Science, 2013, pp. 7143-7152, vol. 54, No. 10.
International Search Report of PCT/KR2019/009457 dated Nov. 11, 2019 [PCT/ISA/210].

* cited by examiner

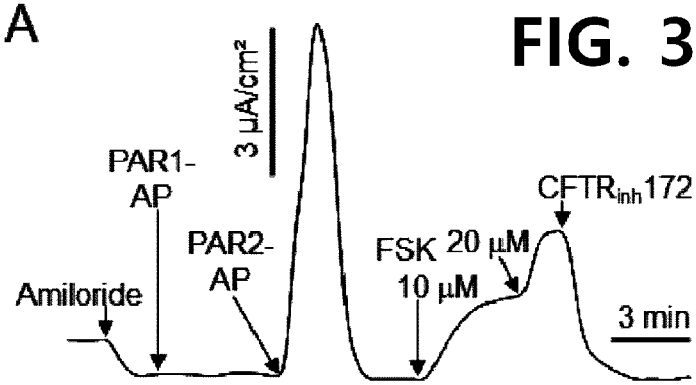
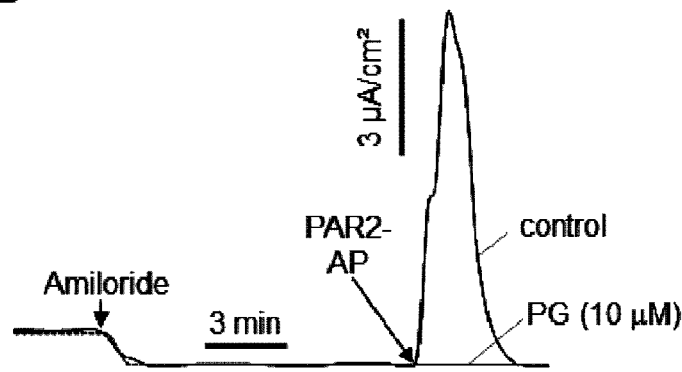
FIG. 3

COMPOSITION COMPRISING PUNICALAGIN FOR INHIBITING PAR2 ACTIVITY

CROSS REFERENCE TO RELATED APPLICATIONS

This application is a National Stage of International Application No. PCT/KR2019/009457 filed on Jul. 30, 2019, claiming priority based on Korean Patent Application No. 10-2018-0088883 filed on Jul. 30, 2018 and Korean Patent Application No. 10-2018-0102307 filed on Aug. 29, 2018, the entire disclosures of which are incorporated herein by reference.

TECHNICAL FIELD

The present invention relates to a composition for inhibiting PAR2 activity including punicalagin, and more specifically, the present invention provides a composition for inhibiting PAR2 activity including punicalagin, a stereoisomer thereof, or a pharmaceutically acceptable salt thereof, or a pharmaceutical composition, health functional food composition, or cosmetic composition for preventing or treating an inflammatory disease or pruritis.

BACKGROUND ART

Protease-activated receptor 2 (PAR2) is one of G protein-coupled receptors (GPCR) that is expressed in a variety of cells such as myocytes, bone cells, neurons, immune cells, epithelial cells, vascular endothelial cells, fibroblasts, and the like. In tissue damage and infection of several inflammatory diseases, PAR2 receptors are activated by being exposed to various in vivo or external serine proteases such as trypsin, tryptase, factor IIVa/Xa, matriptase, kallikreins, granzyme A, histone acetyltransferases (HAT), collagen degrading enzymes (matrix metalloproteinase-1, MMP-1), bacterial serine protease, and the like. Recent research results have shown that when the PAR2 receptor is inhibited in conjunctivitis, colitis, arthritis, dermatitis, gastritis models, and the like, there is an inflammation inhibitory effect.

Punicalagin is ellagitannin, which is a type of phenolic compounds, and it is a natural product contained in pomegranates (*Punica granatum*), Bengal almonds (*Terminalia catappa*), East Indian almonds (*Terminalia myriocarpa*), and South African velvet bushwillows (*Combretum molle*). Punicalagin is a water-soluble compound that hydrolyzes into smaller phenolic compounds such as ellagic acid. Until now, the mechanism of action of punicalagin has not been well known. Studies have been reported that there was no toxicity when rats ingested a 6% punicalagin diet for 37 days, and while it is known that it has inhibitory activity against carbonic anhydrase inhibitors, the mechanism of inhibition of the PAR2 receptor has not been known.

As a result of making intensive efforts to develop a composition capable of preventing or treating an inflammatory disease or pruritus by inhibiting the PAR2 receptor from a natural product-derived substance, the present inventors confirmed that punicalagin specifically inhibits the PAR2 receptor, and the present invention was completed by confirming that punicalagin exhibits an anti-inflammation or pruritis inhibitory effect through the inhibitory mechanism of the PAR2 receptor.

DISCLOSURE

Technical Problem

An object of the present invention is to provide a composition for inhibiting protease-activated receptor 2 (PAR2) activity, including punicalagin, a stereoisomer thereof, or a pharmaceutically acceptable salt thereof.

Another object of the present invention is to provide a pharmaceutical composition for preventing or treating an inflammatory disease or pruritus including the compound.

Still another object of the present invention is to provide a health functional food composition for preventing or ameliorating an inflammatory disease or pruritus including the compound.

Still another object of the present invention is to provide a cosmetic composition for preventing or ameliorating an inflammatory disease or pruritus including the compound.

Technical Solution

The present invention is for solving the above-described problems, and the present invention provides a composition for inhibiting protease-activated receptor 2 (PAR2) activity, including punicalagin, a stereoisomer thereof, or a pharmaceutically acceptable salt thereof.

The composition may a) inhibit an increase in intracellular calcium ions ($Ca^{2+}$) by PAR2 activity; b) inhibit activation of ERK1/2 and NF-κB by PAR2 activity; c) inhibit increased secretion of chloride ions ($Cl^-$) by PAR2 activity; or d) inhibit secretion of a cytokine.

The cytokine may be one or more selected from the group consisting of interferon-gamma (INF-γ), interleukin-β (IL-β), interleukin-2 (IL-2), interleukin-4 (IL-4), interleukin-6 (IL-6), interleukin-8 (IL-8), interleukin-10 (IL-10), interleukin-17A (IL-17A), granulocyte-macrophage colony-stimulating factor (GMCSF), and tumor necrosis factor alpha (TNF-α).

In an embodiment of the present invention, provided is a pharmaceutical composition for preventing or treating an inflammatory disease or pruritus, including punicalagin, a stereoisomer thereof, or a pharmaceutically acceptable salt thereof.

The inflammatory disease or pruritus may be caused by PAR2 activation.

The inflammatory disease may be one or more selected from the group consisting of colitis, conjunctivitis, pancreatitis, lupus nephritis, and atopic dermatitis.

The conjunctivitis may be caused by a house dust mite.

In another embodiment of the present invention, provided is a health functional food composition for preventing or ameliorating an inflammatory disease or pruritus, including punicalagin, a stereoisomer thereof, or a sitologically acceptable salt thereof.

In still another embodiment of the present invention, provided is a cosmetic composition for preventing or ameliorating an inflammatory disease or pruritus, including punicalagin, a stereoisomer thereof, or a cosmetically acceptable salt thereof.

Advantageous Effects

By specifically inhibiting the PAR2 receptor, the composition of the present invention can a) inhibit an increase in intracellular calcium ions ($Ca^{2+}$) by PAR2 activity; b) inhibit activation of ERK1/2 and NF-κB by PAR2 activity; c) inhibit increased secretion of chloride ions ($Cl^-$) by PAR2 activity; or d) inhibit secretion of a cytokine, and through the above, it is possible to prevent or treat various inflammatory diseases or pruritus that are caused by PAR2 receptor activity. In addition, as a plant-derived natural compound, the composition of the present invention can be developed as a novel anti-inflammatory pharmaceutical composition, health functional food composition, and cosmetic composition with less side effects and toxicity.

DESCRIPTION OF DRAWINGS

FIG. 3 is a result of confirming the effect of punicalagin that inhibited $Cl^-$ secretion by PAR2 activity in primary cultured human conjunctival epithelial cells. Panel A of FIG. 3 is a result of measuring $Cl^-$ secretion changes when each inhibitor or activator was treated to determine the level of activities of the ENaC channel, PAR1 receptor, PAR2 receptor, and CFTR channel inhuman conjunctival epithelial cells, and panel B of FIG. 3 is a result of confirming the inhibitory effect of $Cl^-$ secretion by PAR2-AP of punicalagin.

Figure 5:
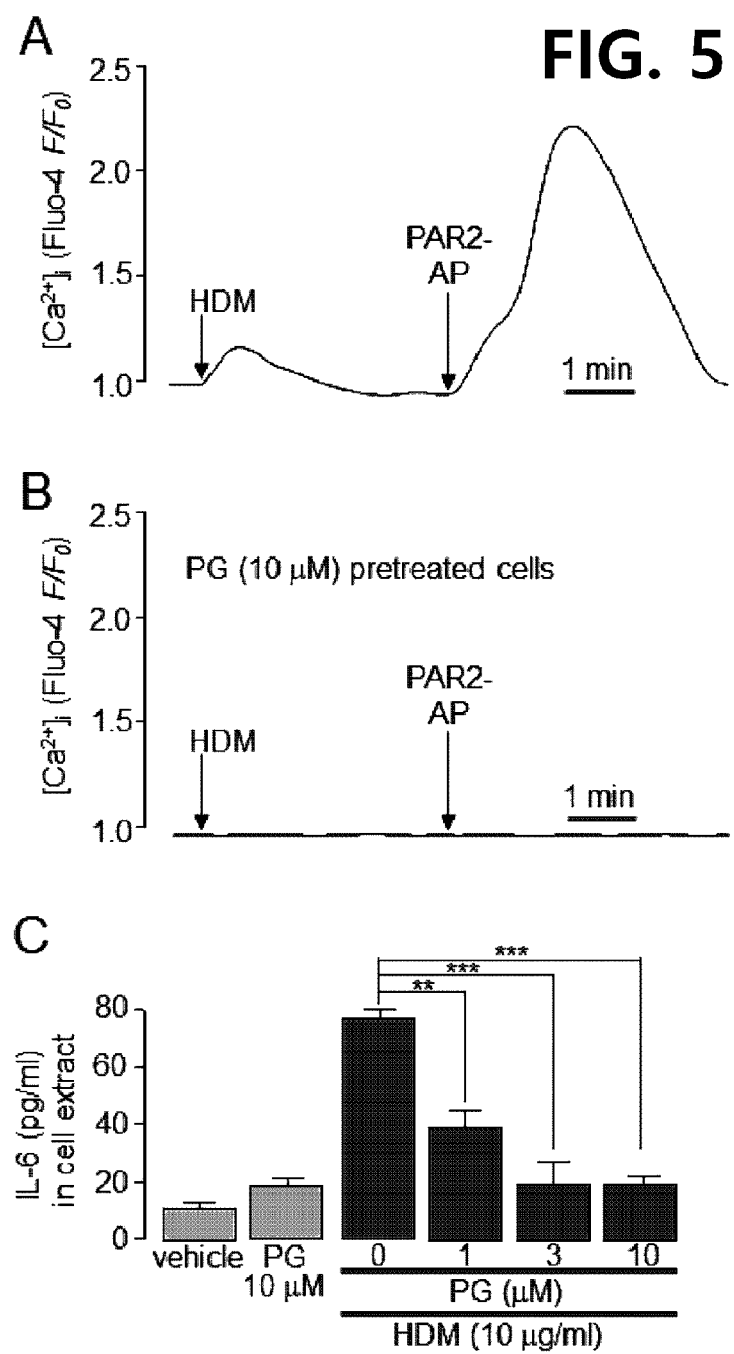

Panel A of FIG. 5 is a result of confirming whether punicalagin inhibited a concentration increase of intracellular calcium ions by a house dust mite (HDM) and PAR2-AP in primary cultured conjunctival epithelial cells, and panel B of FIG. 5 is a result of confirming an effect in which punicalagin inhibited cytokine secretion by HDM treatment. Panel C of FIG. 5 is a result confirming that 1, 3, and 10 μM punicalagin inhibited about 50, 91, and 93% of IL-6 cytokines that were increased by HDM, respectively.

Figure 6:
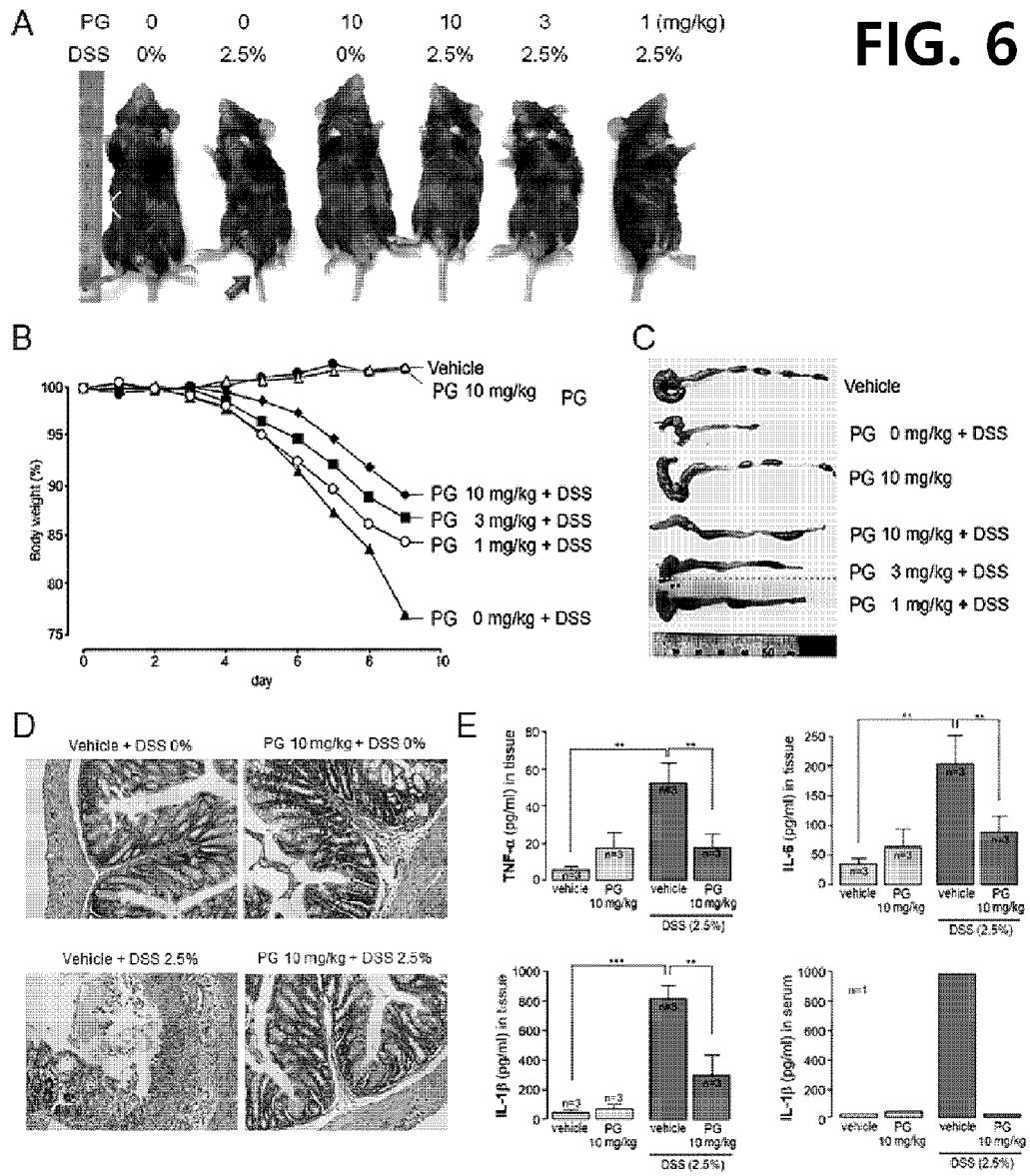

FIG. 6 is a result of confirming whether punicalagin inhibited bloody stool induction (panel A), weight loss (panel B), colon length reduction due to colon inflammation (panel C), colon tissue damage (panel D), and cytokines (panel E) in C57BL6N mice in which colitis was induced by dextran sodium sulfate (DSS).

Figure 7:
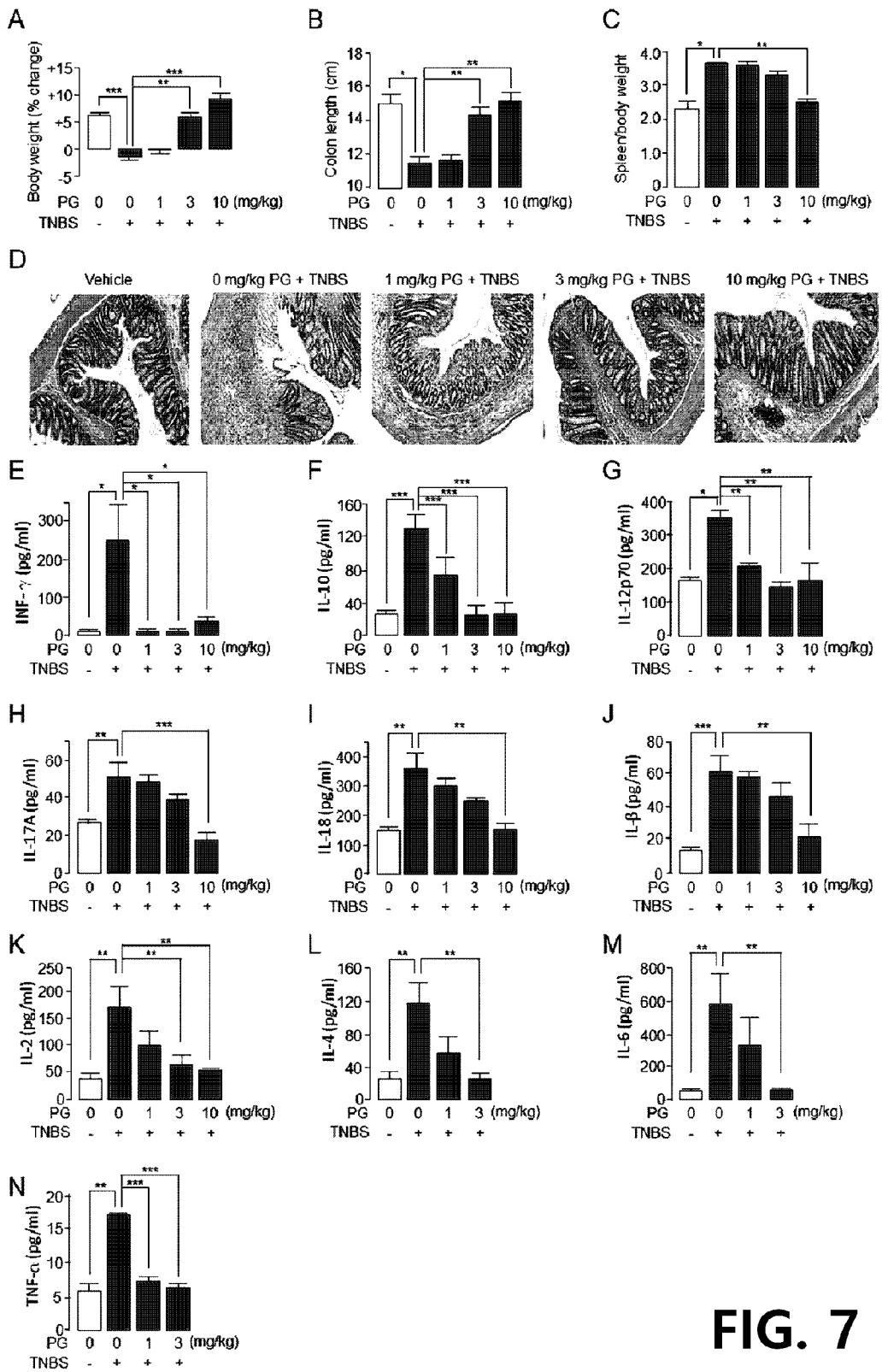

FIG. 7 shows a result of confirming whether punicalagin could ameliorate acute colitis caused by trinitrobenzene sulfonic acid (TNBS) in rats.

Figure 8:
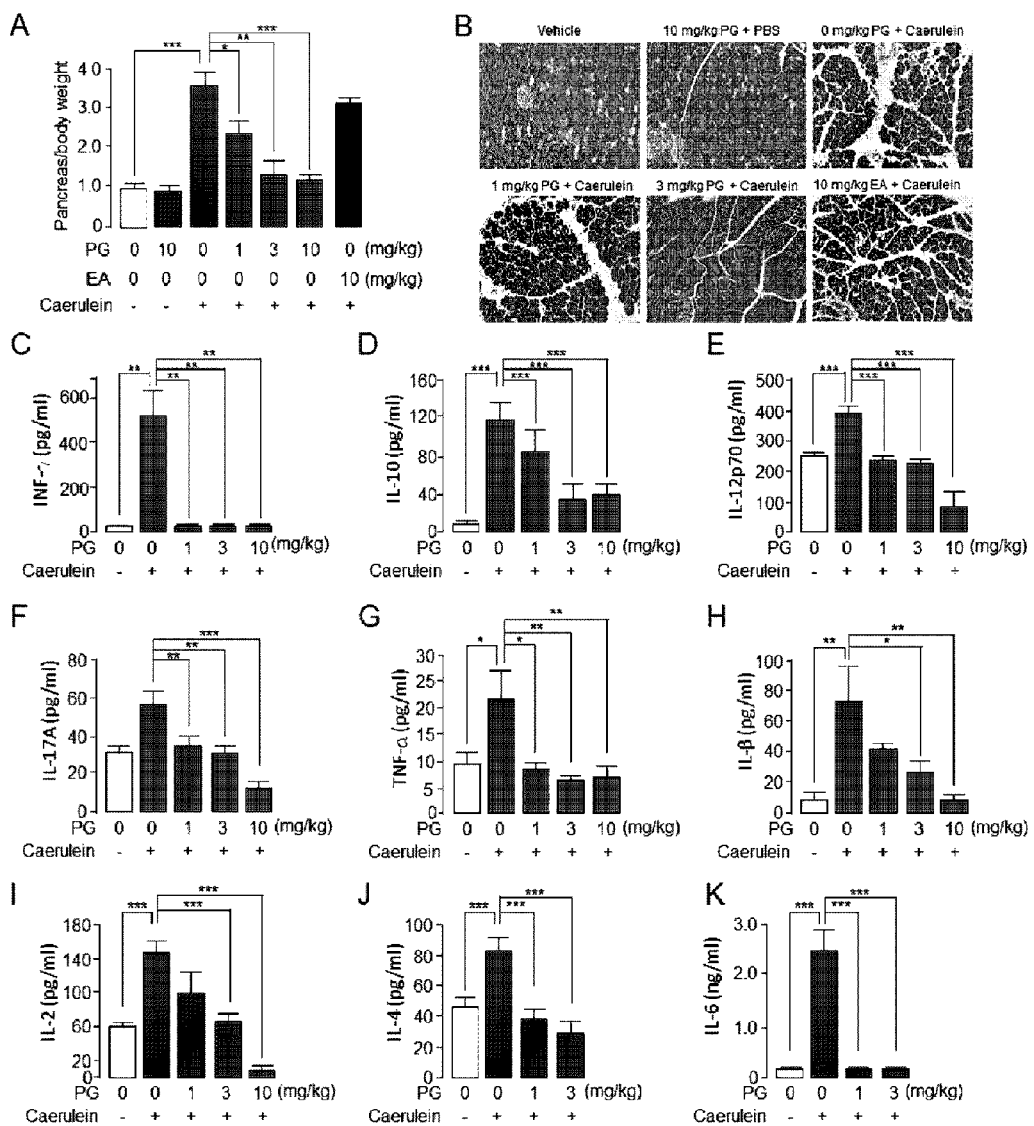

FIG. 8 shows a result of confirming whether punicalagin could ameliorate acute pancreatitis caused by caerulein in rats.

Figure 9:
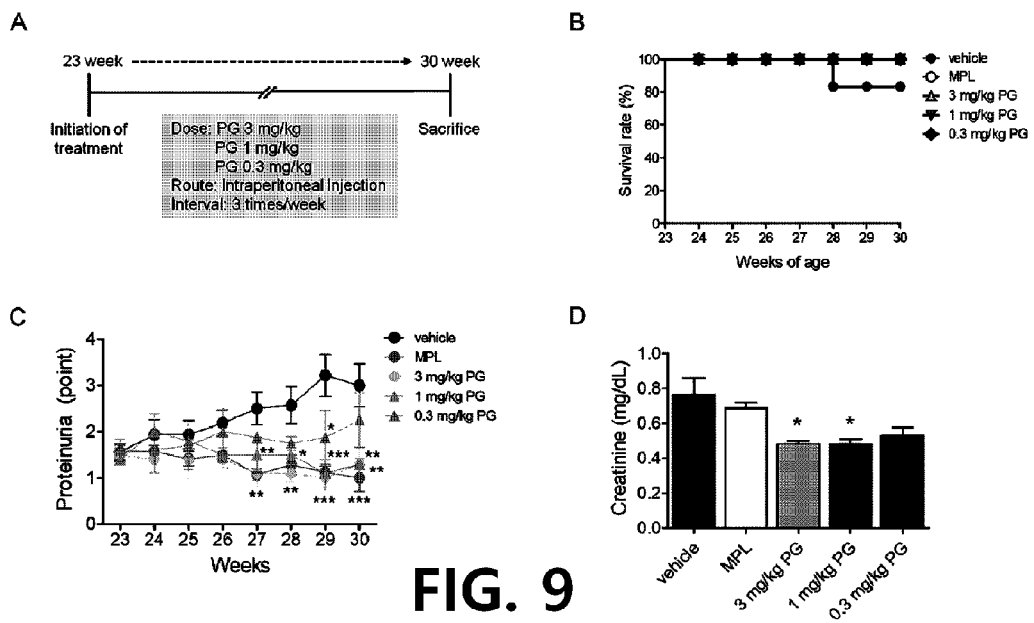

FIG. 9 is a mimetic diagram of an experimental design (panel A) and measurement results of survival rates of experimental animals (panel B), proteinuria amounts (panel C), and serum creatinine concentrations (panel D) for confirming the effect of punicalagin injected into mice in which lupus nephritis was induced.

Figure 10:
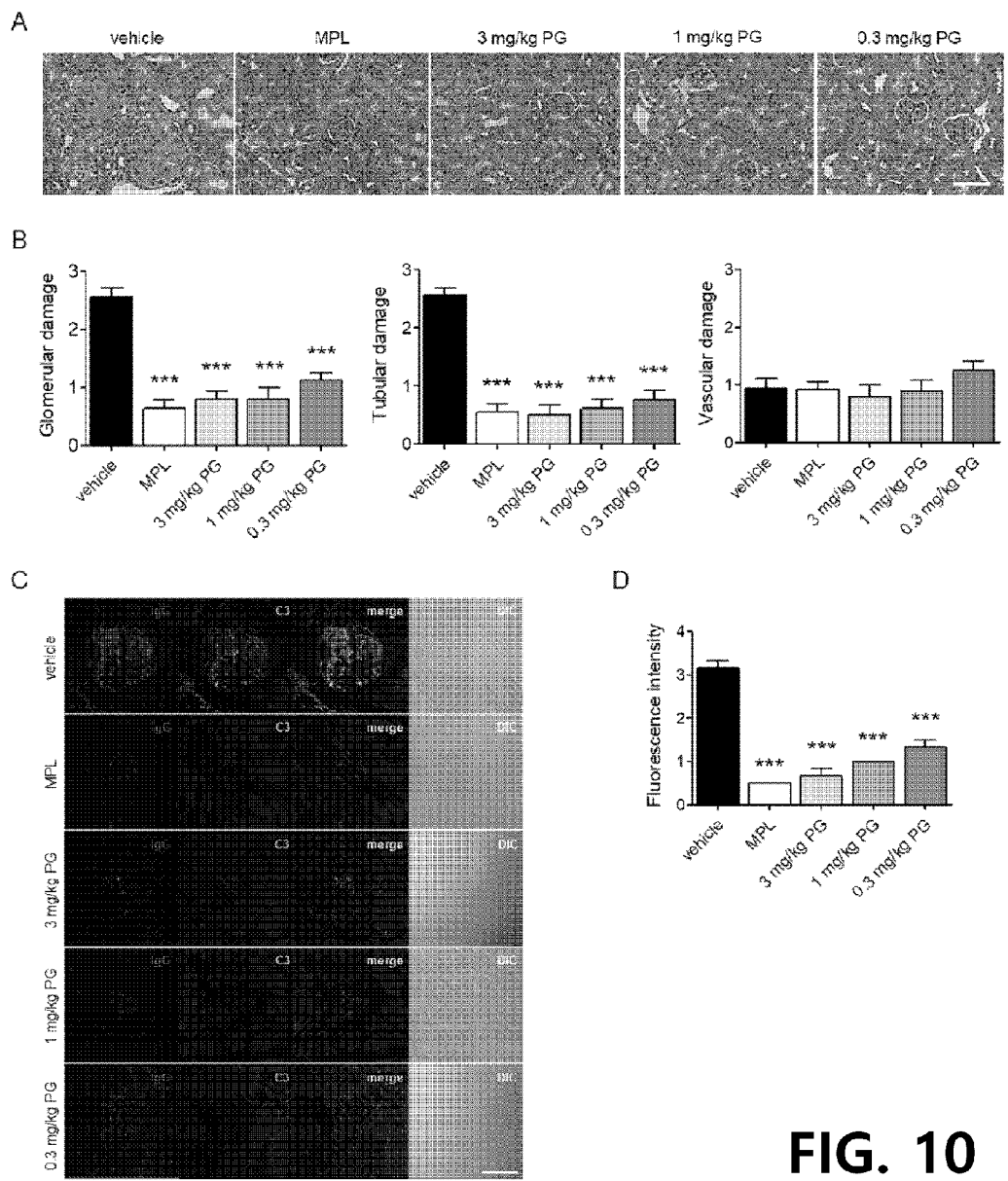

FIG. 10 is a result of confirming the protective effect of punicalagin on kidney tissue in a lupus nephritis mouse model with a microscope (panel A), a result of histologically quantifying the degree of damage to glomeruli, tubules, and blood vessels (panel B), a result of observing autoantibody expression in kidney tissue with a fluorescence microscope (panel C), and a result of quantitatively showing the amount of fluorescence (panel D).

Figure 11:
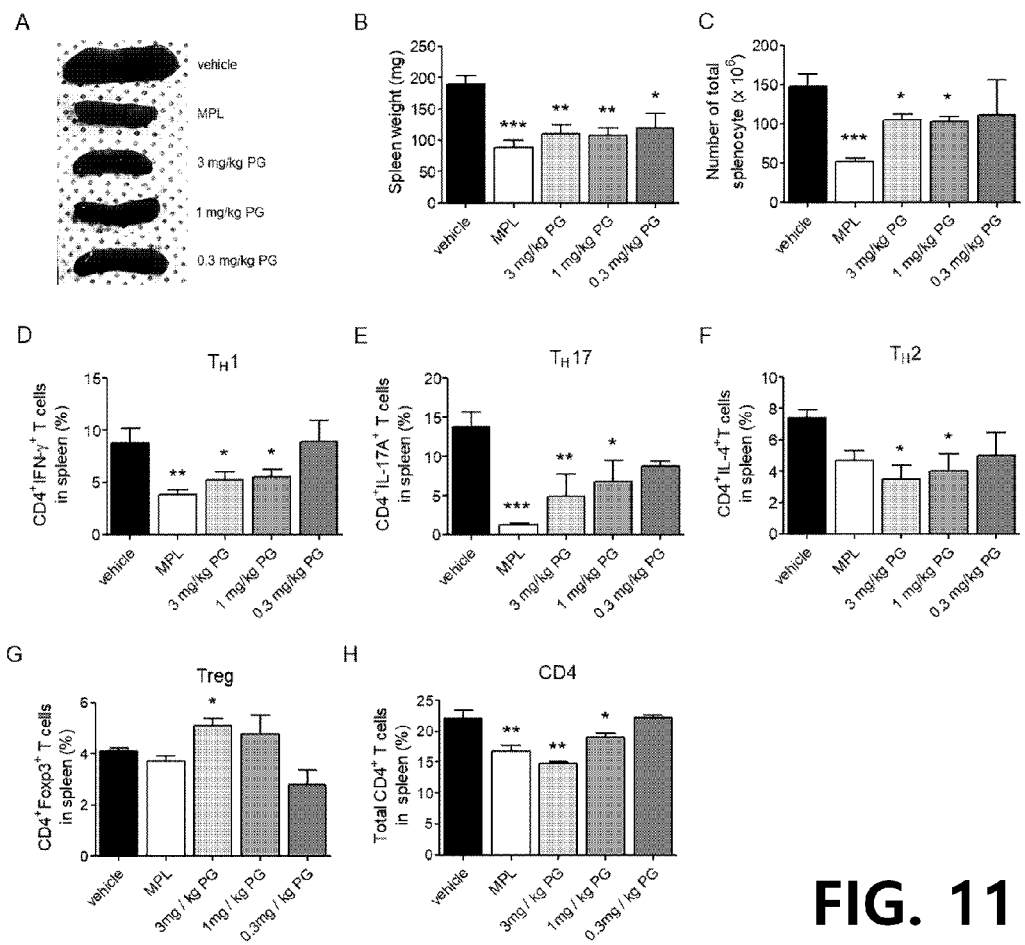

FIG. 11 is a result of measuring spleen weights (panels A and B), spleen cell numbers (panel C), and T cell number changes (panels D to H) that were extracted from the lupus nephritis mouse model.

Figure 12:
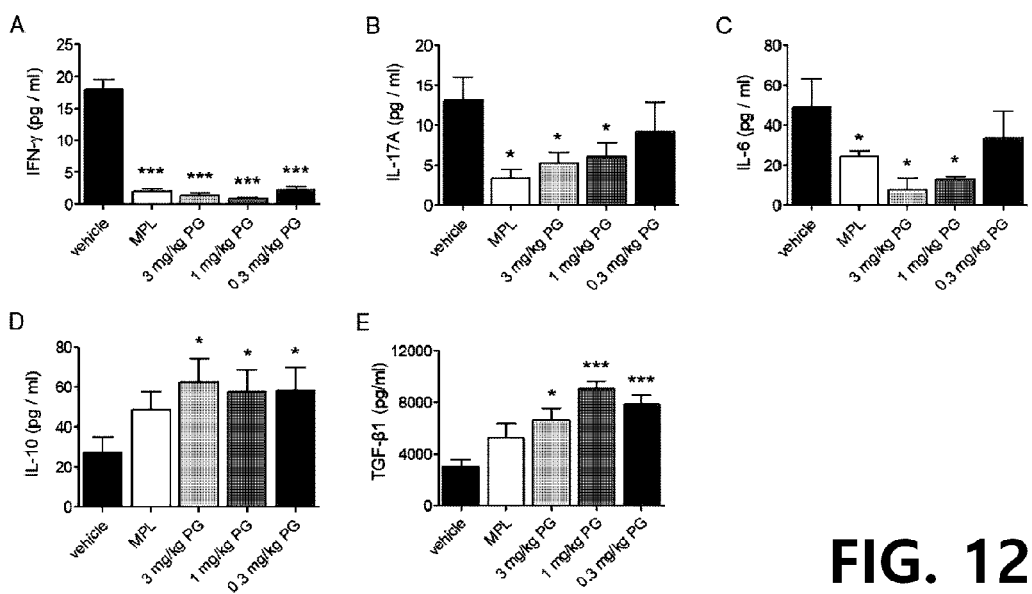

FIG. 12 is a result of confirming the inflammatory cytokine concentrations (panels A to C) and the anti-inflammatory cytokine concentrations (panels D and E) of the serum of the lupus nephritis mouse model.

Figure 13:
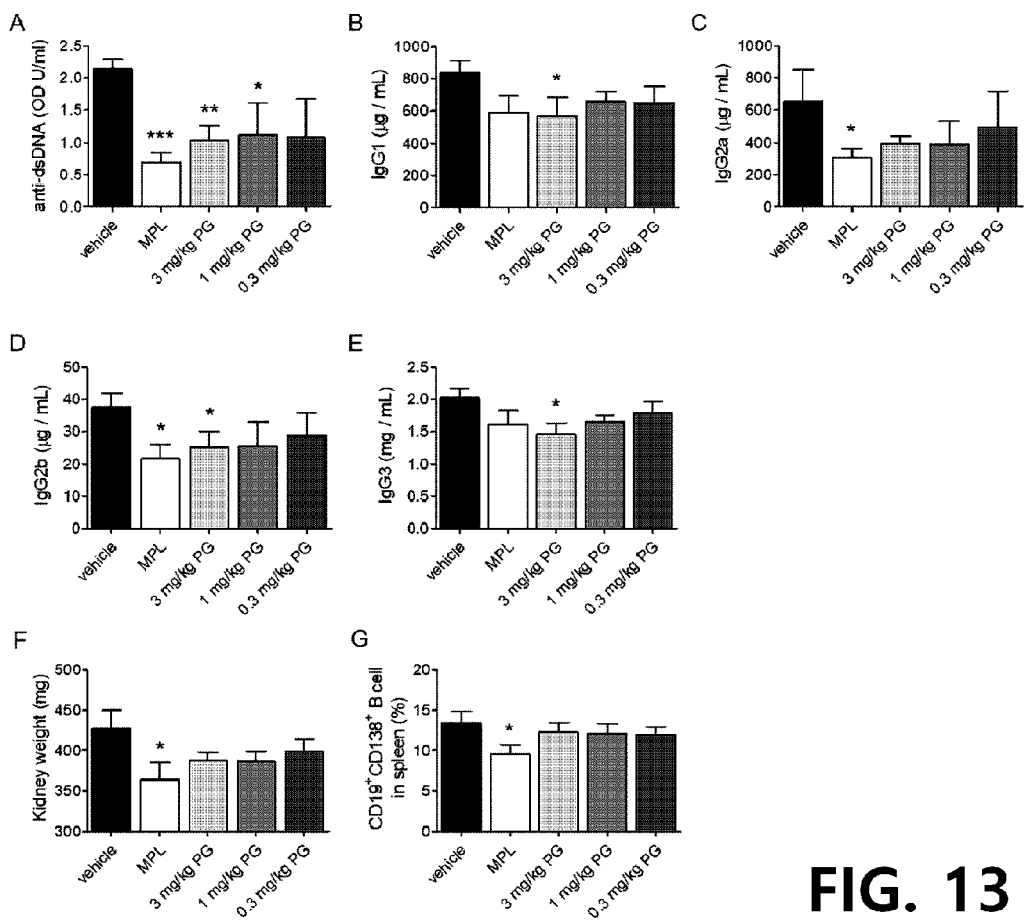

FIG. 13 is a result of measuring blood B cell antibody changes (panels A to E), kidney weights (panel F), and cell changes (panel G) in the lupus nephritis mouse model.

Figure 14:
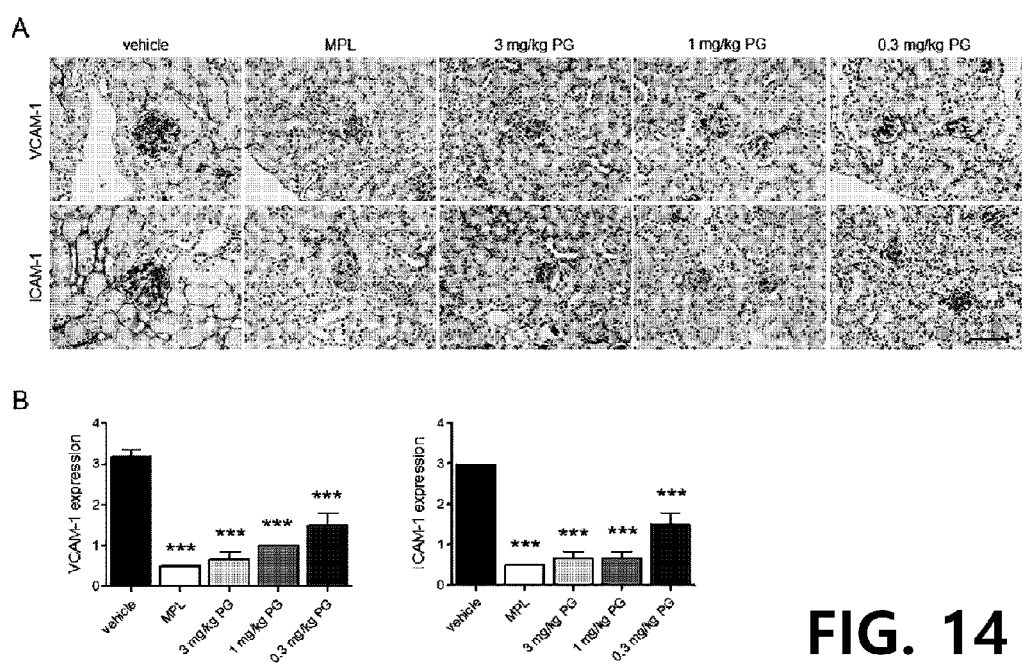

FIG. 14 is a result of the expressions of VCAM-1 and ICAM-1 (panel A) and the quantified degree of expression (panel B) in kidney tissue of the lupus nephritis mouse model.

Figure 15:
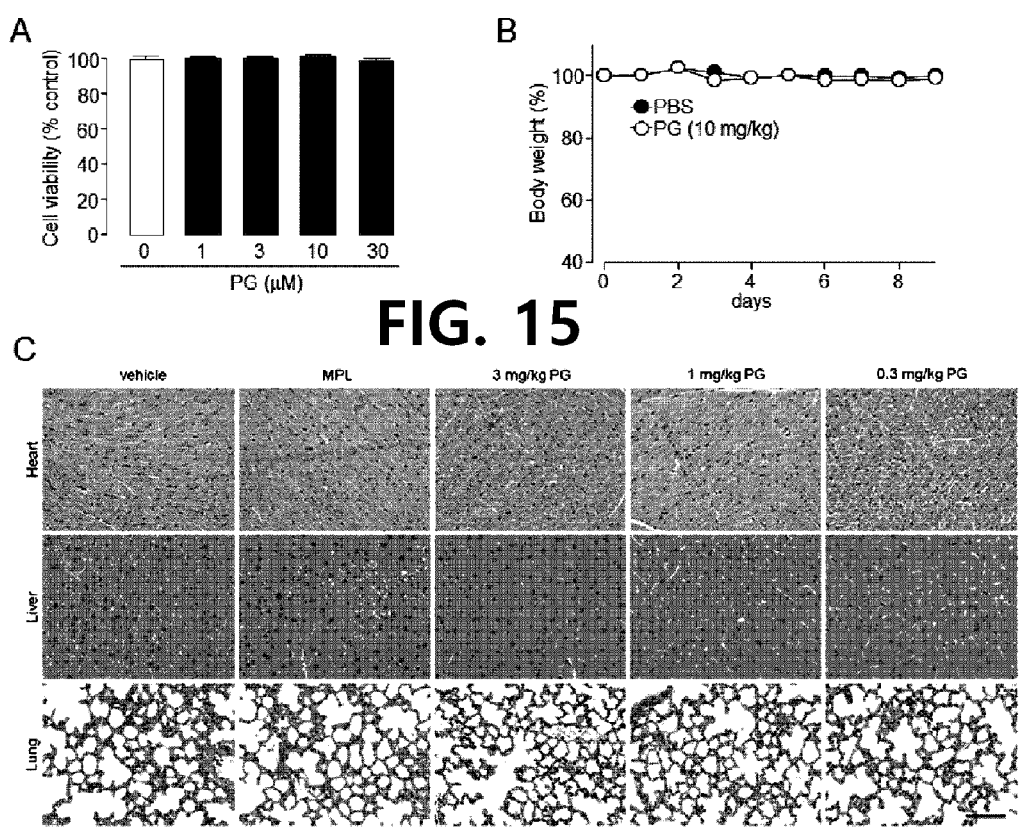

FIG. 15 is a result of confirming the changes in cell viability by punicalagin (panel A), the weight changes of mice (panel B), and the effect on the tissues in heart, liver, and lung tissues of the lupus nephritis mouse model (panel C).

Figure 16:
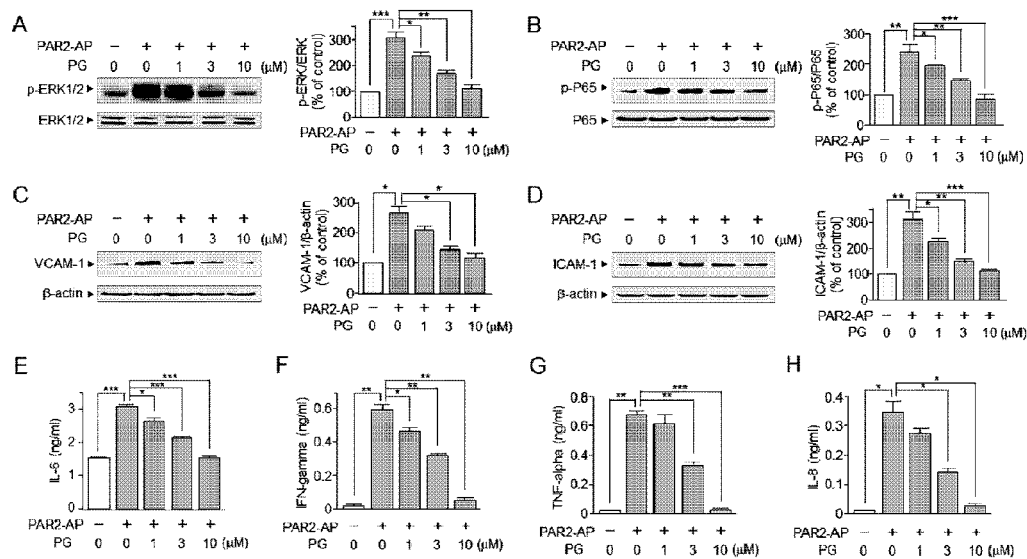

FIG. 16 is a result of confirming the effect of punicalagin on cellular signal changes and inflammatory cytokine secretion by PAR2 receptor activity in human glomerular podocytes.

Figure 17:
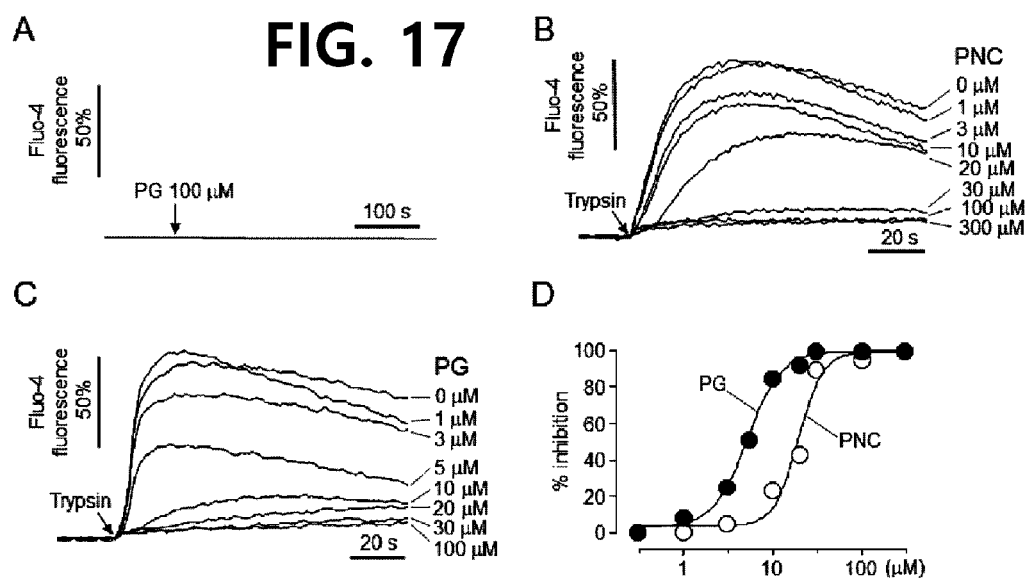

FIG. 17 is a result of confirming the effect of inhibiting an increase in the concentration of intracellular calcium ions depending on PAR2 receptor activity by trypsin in HaCaT cells which are human keratinocyte lines by punicalin (PNC) or punicalagin (PG) according to an exemplary embodiment of the present invention.

Figure 18:
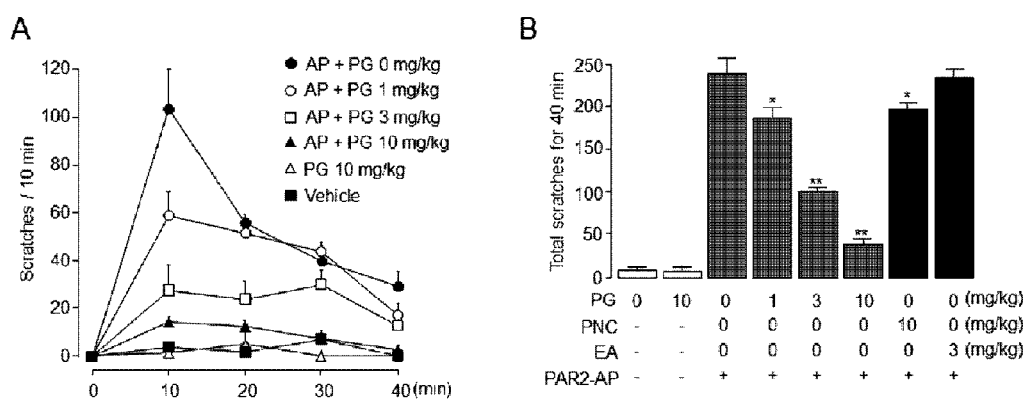

FIG. 18 is a result of confirming whether punicalagin, punicalin, or ellagic acid (EA) inhibited pruritus in C57BL6N mice in which pruritus was induced by the PAR2 receptor activating peptide (PAR2-activating peptide, AP).

Figure 19:
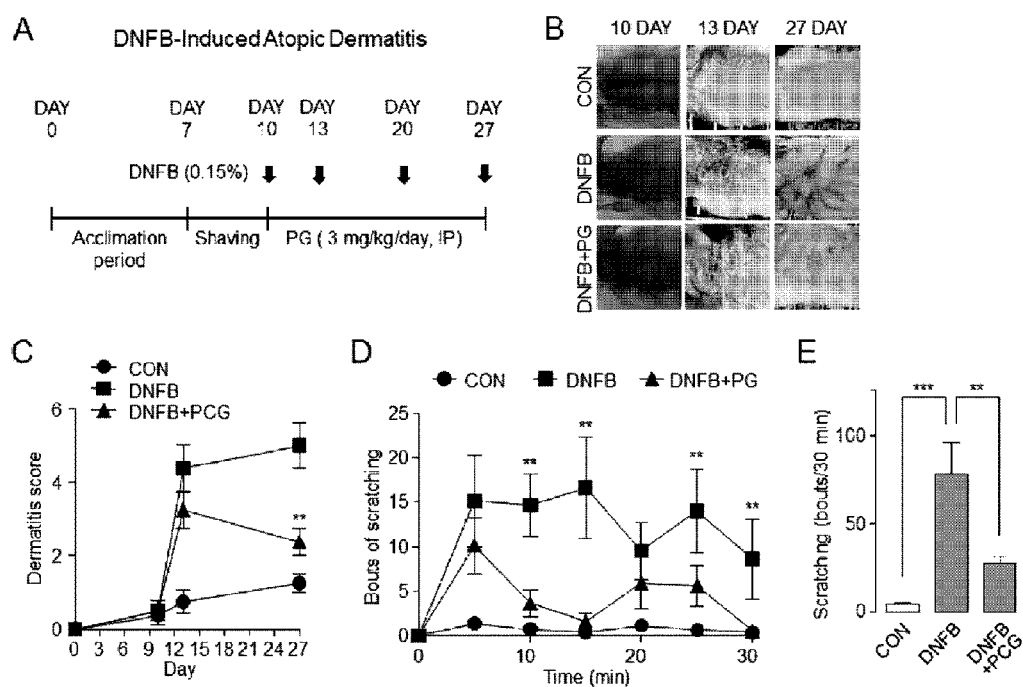

FIG. 19 is a result of confirming whether punicalagin inhibited atopic dermatitis and pruritus in an atopic dermatitis model induced by 1-fluoro-2,4-dinitrobenzene (DNFB).

MODES OF THE INVENTION

The present inventors searched a compound library provided by the Korea Chemical Bank to develop new drugs from natural products for treating inflammation or inhibiting pruritus, and conducted molecular physiological experiments to discover that punicalin inhibits the PAR2 receptor. Knowing that punicalin has a relatively weak inhibitory effect on the PAR2 receptor, efforts have been made to discover superior natural product compounds. As a result, the present invention was completed by confirming that punicalagin, which is an analogue of punicalin, specifically inhibits the activity of the PAR2 receptor, and in addition to inhibiting cytokines secreted from inflammation of primary cultured human conjunctival epithelium, it alleviates symptoms caused by colitis (particularly, colitis caused by DSS or TNBS), acute pancreatitis (particularly, acute pancreatitis caused by caerulein), lupus nephritis, or atopic dermatitis/ pruritus (particularly, pruritus caused by DNFB) induced in animal model experiments through specific experiments.

Meanwhile, it was confirmed that ellagic acid, which is a metabolite of punicalagin and one of the main components of pomegranate peel, does not inhibit the activity of the PAR2 receptor, and it cannot alleviate symptoms caused by acute pancreatitis induced in animal model experiments (particularly, acute pancreatitis induced by caerulein) or pruritus induced by PAR2-AP.

Hereinafter, the present invention will be described in detail.

The present invention provides a composition for inhibiting protease-activated receptor 2 (PAR2) activity, including punicalagin represented by Chemical Formula below, a stereoisomer thereof, or a pharmaceutically acceptable salt thereof.

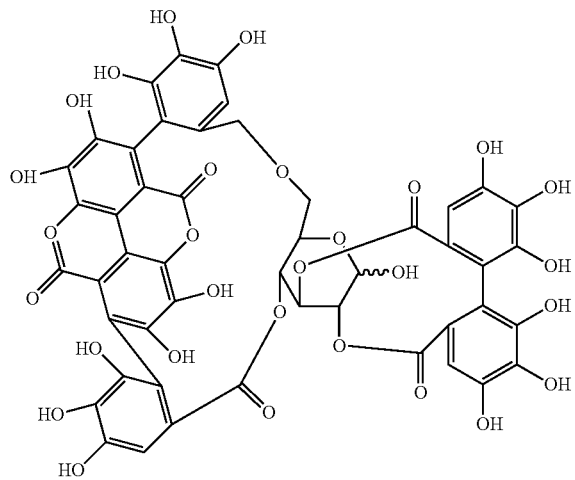

Specifically, the punicalagin is a component mainly contained in pomegranates (particularly, pomegranate peel), the structural formula is $C_{48}H_{28}O_{30}$, and the molecular weight is 1,084.71 g/mol. The CAS number is 65995-63-3, and the IUPAC name is 1,2,3,11,12,13-hexahydroxy-5,10-dioxo-8-[3,4,5,11,17,18,19,22,23,34,35-undecahydroxy-8,14,26,31-tetraoxo-9,13,25,32-tetraoxaheptacyclo[25.8.0.0$^{2,7}$.0$^{15,20}$.0$^{21,30}$.0$^{24,29}$.0$^{28,33}$]pentatnaconta-1(35),2,4,6,15,17,19,21,23,27,29,33-dodecaen-10-yl]-5,7,8,10-tetrahydrodibenzo[f,h][1,4]dioxecin-7-carbaldehyde.

Punicalagin of the present invention may include a punicalagin hydrate, a punicalagin derivative, and the like within the range having the same efficacy as the punicalagin, and may also include a solvent compound or stereoisomer thereof.

The method for obtaining the punicalagin is not particularly limited, and it is possible to isolate from plants containing the punicalagin, chemically synthesize using a known preparation method, or use a commercially available product.

As used herein, the terms "a pharmaceutically acceptable salt", "a sitologically acceptable salt", "a cosmetically acceptable salt", or "a salt thereof" may be an acid addition salt formed by free acid. The acid addition salt may be obtained from inorganic acids such as hydrochloric acid, nitric acid, phosphoric acid, sulfuric acid, hydrobromic acid, hydroiodic acid, nitrous acid, or phosphorous acid, and non-toxic organic acids such as aliphatic mono and dicarboxylates, phenyl-substituted alkanoates, hydroxy alkanoates and alkandioates, aromatic acids, aliphatic and aromatic sulfonic acids. Such pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butine-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, or mandelate.

The acid addition salt according to the present invention may be prepared by a conventional method, for example, by dissolving the compound in an excess aqueous acid solution and precipitating the salt using a water-miscible organic solvent, for example, methanol, ethanol, acetone, or acetonitrile. The same amount of the compound and acid or alcohol in water may be heated, and then, the mixture may be evaporated for drying or prepared by suction filtration of the precipitated salt.

In addition, bases may be used to make a pharmaceutically acceptable metal salt. Alkali metal or alkaline earth metal salts are obtained, for example, by dissolving a compound in an excess of an alkali metal hydroxide or alkaline earth metal hydroxide solution, filtering the insoluble compound salt, and evaporating and drying the filtrate. In this case, it is pharmaceutically suitable to prepare a sodium, potassium, or calcium salt as the metal salt. In addition, silver salts corresponding thereto are obtained by reacting alkali metal or alkaline earth metal salts with a suitable silver salt (e.g., silver nitrate).

In addition, the compound of the present invention includes not only pharmaceutically acceptable salts, but also all salts, hydrates, and solvates that can be prepared by conventional methods.

The addition salt according to the present invention may be prepared by a conventional method, for example, by dissolving the compound in a water-miscible organic solvent, for example, acetone, methanol, ethanol, or acetonitrile, and adding an excess of an organic acid or acid aqueous solution of an inorganic acid, followed by precipitation or crystallization. Next, the solvent or excess acid may be evaporated and dried in this mixture to obtain an addition salt, or the precipitated salt may be prepared by suction filtration.

As used herein, the term "PAR2 activity inhibitor" or "PAR2 inhibitor" refers to a substance capable of inhibiting or reducing the metabolic action of PAR2 in vivo by inhibiting the active action thereof, when the PAR2 receptor is activated by trypsin, PAR2-AP, and the like.

The PAR2 activity inhibitor composition of the present invention may block or mitigate the action exhibited through PAR2 activity. Specifically, the composition of the present invention may specifically inhibit an increase in intracellular calcium ions ($Ca^{2+}$) and ERK1/2 and NF-κB activations by PAR2 activity. In addition, the composition of the present invention may reduce increased secretion of chloride ions ($Cl^-$) by inhibiting the activity of the calcium-activated chloride channel (CaCC) by PAR2 activity. In addition, the composition of the present invention may inhibit the secretion of a cytokine by PAR2 activity. The cytokine may be selected from the group consisting of interferon-gamma (INF-γ), interleukin-β (IL-β), interleukin-2 (IL-2), interleukin-4 (IL-4), interleukin-6 (IL-6), interleukin-8 (IL-8), interleukin-10 (IL-10), interleukin-17A (IL-17A), granulocyte-macrophage colony-stimulating factor (GMCSF), and tumor necrosis factor alpha (TNF-α), but it is not limited as long as it is a cytokine that is secreted by PAR2 activity.

The present invention also provides a pharmaceutical composition for preventing or treating an inflammatory disease or pruritus including the compound or a pharmaceutically acceptable salt thereof as an active ingredient.

The "inflammatory disease or pruritus" of the present invention may be caused by PAR2 activation, and specifically, it may be a disease or symptom caused by the secretion of inflammatory cytokines due to the activity of PAR2.

Specifically, the inflammatory disease may be one or more selected from the group consisting of colitis, conjunctivitis, pancreatitis, lupus nephritis, and dermatitis (particularly, atopic dermatitis). In this case, the colitis may include both ulcerative colitis and Crohn's disease, the conjunctivitis may be caused by a house dust mite, and the pancreatitis may be acute pancreatitis, in particular, acute edema or hemorrhagic pancreatitis. In addition, the lupus nephritis may be systemic erythematosus lupus nephritis, which is a chronic autoimmune disease, and it may be lupus nephritis in patients with the activation of vascular cell adhesion molecule 1 (VCAM-1) or intercellular adhesion molecule 1 (IMC-1). Herein, VCAM-1 or ICAM-1 may play a role in collecting leukocytes such as neutrophils, macrophages, and the like at a site of inflammation in lupus nephritis. In addition, the pruritus refers to a skin disease symptom accompanied by severe pain by increasing the feeling to be scratched in eczema, dermatitis, urticaria, and similar diseases, and may include both pruritus accompanied by dermatitis and pruritus without dermatitis. In addition, it specifically includes all itching caused by one or more diseases selected from the group consisting of allergic dermatitis, atopic dermatitis, contact dermatitis, acne, seborrheic dermatitis, urticaria, and psoriasis.

More specifically, the prophylactic or therapeutic effect of colitis may be confirmed through ulcerative colitis animal model experiments induced by DSS or through Crohn's disease-like animal model experiments induced by TNBS. In addition, the prophylactic or therapeutic effect of pancreatitis may be confirmed through animal model experiments of acute edema pancreatitis induced by caerulein. In addition, the prophylactic or therapeutic effect of pruritus may be confirmed through pruritus animal model experiments without dermatitis caused by PAR2 activation or pruritus animal model experiments with dermatitis caused by DNFB.

The composition of the present invention may prevent the inflammatory disease or pruritus, and alleviate or treat symptoms by inhibiting the activity of PAR2.

The pharmaceutical composition of the present invention may further include a pharmaceutically acceptable carrier, in addition to containing the compound as an active ingredient.

As used herein, the term "pharmaceutically acceptable" means that it is conventionally used in the pharmaceutical field, without stimulating the organism upon administration thereof, and without inhibiting the biological activity and properties of the compound to be administered.

The pharmaceutical composition of the present invention may be formulated with the carrier and used as food, medicine, feed additives, drinking water additives, and the like. In the present invention, the type of the carrier is not particularly limited, and any carrier may be used as long as it is a conventionally used carrier in the corresponding technical field. Non-limiting examples of the carrier include saline, sterile water, Ringer's solution, buffered saline, albumin injection solutions, lactose, dextrose, sucrose, sorbitol, mannitol, xylitol, erythritol, maltitol, maltodextrin, glycerol, ethanol, and the like. These may be used alone or in combination of two or more thereof.

In addition, the pharmaceutical composition of the present invention may be used, if necessary, by adding other pharmaceutically acceptable additives such as excipients, diluents, antioxidants, buffers, bacteriostatic agents, or the like, and fillers, extenders, wetting agents, disintegrants, dispersants, surfactants, binders, lubricants, or the like may be additionally added and used.

The pharmaceutical composition of the present invention may be formulated and used in a variety of formulations suitable for oral or parenteral administration. Non-limiting examples of the formulation for oral administration may include troches, lozenges, tablets, aqueous suspensions, oily suspensions, prepared powders, granules, emulsions, hard capsules, soft capsules, syrups, elixirs, or the like.

In order to formulate the pharmaceutical composition of the present invention for oral administration, binders such as lactose, saccharose, sorbitol, mannitol, starch, amylopectin, cellulose, gelatin, or the like; excipients such as dicalcium phosphate or the like; disintegrants such as corn starch, sweet potato starch, or the like; lubricants such as magnesium stearate, calcium stearate, sodium stearyl fumarate, polyethylene glycol wax, or the like may be used, and sweeteners, fragrances, syrups, and the like may also be used.

Furthermore, in the case of capsules, liquid carriers such as fatty oil and the like may be additionally used in addition to the above-mentioned substances.

Non-limiting examples of the formulation for parenteral administration include injection liquids, suppositories, respiratory inhalation powders, spray aerosols, ointments, application powders, oils, creams, and the like.

In order to formulate the pharmaceutical composition of the present invention for parenteral administration, sterile aqueous solutions, non-aqueous solvents, suspensions, emulsions, lyophilized formulations, external preparations, and the like may be used. For the non-aqueous solvents and suspensions, propylene glycol, polyethylene glycol, vegetable oils such as olive oil, injectable esters such as ethyl oleate and the like may be used.

In addition, more specifically, when the pharmaceutical composition of the present invention is formulated into an injection solution, the composition of the present invention may be mixed with water with a stabilizer or buffer to prepare a solution or suspension, which is then formulated for unit administration of an ampoule or vial. In addition, when the pharmaceutical composition of the present invention is formulated into an aerosol, propellants and the like may be combined with an additive to disperse a water-dispersed concentrate or wet powder.

In addition, when the pharmaceutical composition of the present invention is formulated into an ointment, a cream, and the like, animal oil, vegetable oil, wax, paraffin, starch, tragacanth, cellulose derivatives, polyethylene glycol, silicone, bentonite, silica, talc, zinc oxides, and the like may be used as a carrier for formulation.

A pharmaceutically effective amount and effective dosage of the pharmaceutical composition of the present invention may be varied by the method of formulating the pharmaceutical composition, the mode of administration, the time of administration, and/or the route of administration. In addition, it may be varied depending on various factors such as the type and extent of reactions to be achieved by administration of the pharmaceutical composition, the type of a subject to be administered, age, weight, general status of health, condition or extent of disease, sex, diet, excretion, drugs used simultaneously or currently for the corresponding subject, components of other compositions, and the like, and similar factors well known in the medical field. In addition, those of ordinary skill in the corresponding technical field may easily determine and prescribe an effective dosage for the desired treatment.

The dosage for the more preferred effect of the pharmaceutical composition of the present invention may be preferably 0.1 mg/kg to 1,000 mg/kg per day, and more preferably, 10 mg/kg to 500 mg/kg per day. The administration of the pharmaceutical composition of the present invention may be administered once a day, or may be administered several times. Therefore, the above dosage does not limit the scope of the present invention in any aspect.

The administration route and administration mode of the pharmaceutical composition of the present invention may be independent of each other, and are not particularly limited in the manner, and any administration route and administration mode may be followed as long as the pharmaceutical composition may reach the desired corresponding site. The pharmaceutical composition may be administered by oral administration or parenteral administration.

As the method for parenteral administration, for example, intravenous administration, intraperitoneal administration, intramuscular administration, transdermal administration, or subcutaneous administration may be used, and a method of applying, spraying, or inhaling the composition to a diseased area may also be used, but is not limited thereto.

The present invention also provides a health functional food composition for preventing or ameliorating an inflammatory disease or pruritus including the compound or a sitologically acceptable salt thereof.

As used herein, the term "health functional food" refers to food prepared and processed in the form of tablets, capsules, powders, granules, liquids, pills, and the like, using raw materials or ingredients having useful functions for the human body. Herein, the term 'functional' means to obtain a useful effect for health purposes such as nutrient control, physiological action, and the like on the structure and function of the human body. The health functional food of the present invention may be prepared by a method conventionally used in the art, and upon the preparation, it may be prepared by adding raw materials and ingredients conventionally added in the art. In addition, the formulation of the health functional food may also be prepared without limitation as long as the formulation is recognized as health functional food. The health functional food composition of the present invention has an advantage of having no side effects and the like that may occur during a long-term use of drugs, unlike general drugs, because food is used as the raw material, and it is excellent in portability and may be consumed as an adjuvant to enhance the anti-inflammatory effect.

In the anti-inflammatory health functional food according to the present invention, when using the punicalagin as an additive of the health functional food, it may be added as it is or used with other foods or food ingredients, and it may be appropriately used according to a conventional method. The mixed amount of the active ingredient may be appropriately determined depending on the purpose of use, such as prevention, health, therapy, or the like.

The formulation of health functional food may be in the form of powders, granules, pills, tablets, or capsules, as well as in the form of general foods or beverages.

The type of the food is not particularly limited, and examples of food to which the above substance may be added include meat, sausage, bread, chocolate, candy, snacks, confectionery, pizza, ramen, other noodles, gum, dairy products including ice cream, various soups, beverages, teas, drinks, alcoholic beverages, vitamin complexes, and the like, and may include all foods in the conventional meaning.

In general, upon preparation of food or beverages, the punicalagin may be added at an amount of 15 parts by weight or less, and preferably, 10 parts by weight or less, based on 100 parts by weight of the raw material. However, in the case of long-term intake for the purpose of health and hygiene or for the purpose of health control, the amount may be within the above range or less. In addition, since the present invention has no problem in terms of safety in that fractions from natural products are used, the amount within the above range or more may also be used.

In the functional food according to the present invention, the beverage may contain various flavors, natural carbohydrate, or the like as an additional component as in conventional beverages. The natural carbohydrate described above may be monosaccharides such as glucose and fructose, disaccharides such as maltose and sucrose, polysaccharides such as dextrin and cyclodextrin, sugar alcohols such as xylitol, sorbitol, erythritol, and the like. As a sweetener, natural sweeteners such as thaumatin and stevia extracts, or synthetic sweeteners such as saccharin and aspartame, and the like may be used. The ratio of the natural carbohydrate may be about 0.01 g to 0.04 g per 100 mL of the beverage and preferably, about 0.02 g to 0.03 g per 100 mL of the beverage according to the present invention.

In addition to the above, the anti-inflammatory health functional food according to the present invention may contain various nutrients, vitamins, electrolytes, flavoring agents, coloring agents, pectic acid and a salt thereof, alginic acid and a salt thereof, organic acids, protective colloid thickeners, pH regulators, stabilizers, preservatives, glycerin, alcohols, and carbonating agents used in carbonated drinks. In addition, the anti-inflammatory health functional food composition of the present invention may contain pulp for the production of natural fruit juice, fruit juice beverages and vegetable beverages. These components may be used independently or in combination. The ratio of such additives is not limited, but it is generally selected from a range of 0.01 parts by weight to 0.1 parts by weight based on 100 parts by weight of the functional food of the present invention.

The present invention also provides a cosmetic composition for preventing or ameliorating an inflammatory disease or pruritus including the compound or a cosmetically acceptable salt thereof.

The components included in the cosmetic composition of the present invention include components conventionally used in cosmetic compositions in addition to the above compound or a cosmetically acceptable salt thereof as an active ingredient, and for example, antioxidants, stabilizers, solubilizers, vitamins, conventional adjuvants such as pigments and fragrances, and carriers may be included.

The cosmetic composition of the present invention may be prepared in any formulation conventionally prepared in the art and may be formulated into, for example, solutions, suspensions, emulsions, pastes, gels, creams, lotions, powders, soaps, surfactant-containing cleansers, oils, powder foundations, emulsion foundations, wax foundations, sprays, and the like, but is not limited thereto.

When the formulation of the present invention is a paste, cream, or gel, animal oil, vegetable oil, wax, paraffin, starch, tragacanth, cellulose derivatives, polyethylene glycol, silicone, bentonite, silica, talc, or zinc oxide may be used as a carrier component.

When the formulation of the present invention is a powder or spray, lactose, talc, silica, aluminum hydroxide, calcium silicate, or polyamide powder may be used as a carrier component, and particularly in the case of a spray, it may additionally include propellants such as chlorofluorohydrocarbon, propane/butane, or dimethyl ether.

When the formulation of the present invention is a solution or emulsion, solvents, solubilizing agents, or emulsifying agents may be used as a carrier component, and for example, there are water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

When the formulation of the present invention is a suspension, liquid diluents such as water, ethanol, or propylene glycol, suspending agents such as ethoxylated isostearyl alcohol, polyoxyethylene sorbitol ester, and polyoxyethylene sorbitan ester, microcrystalline cellulose, aluminum metahydroxide, bentonite, agar, tragacanth, or the like may be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamido betaine, aliphatic alcohols, fatty acid glyceride, fatty acid diethanolamide, vegetable oil, lanolin derivatives, ethoxylated glycerol fatty acid esters, or the like may be used as a carrier component.

Furthermore, the present invention provides a use for using a pharmaceutical composition for preventing or treating an inflammatory diseases or pruritus, including punicalagin, a stereoisomer thereof, or a pharmaceutically acceptable salt thereof.

In addition, the present invention provides a use for using a health functional food composition for preventing or ameliorating an inflammatory disease or pruritus, including punicalagin, a stereoisomer thereof, or a sitologically acceptable salt thereof.

In addition, the present invention provides a use for using a cosmetic composition for preventing or ameliorating an inflammatory disease or pruritus, including punicalagin, a stereoisomer thereof, or a cosmetically acceptable salt thereof.

In addition, the present invention provides a method for preventing or treating an inflammatory disease or pruritus, including administering punicalagin, a stereoisomer thereof, or a pharmaceutically acceptable salt thereof to a subject.

As used herein, the term "subject" refers to a subject in need of treatment for a disease, and more specifically, it refers to humans or non-human primates, and mammals such as mice, rats, dogs, cats, horses, cows, and the like.

Hereinafter, the present invention will be described in more detail through exemplary embodiments. These exemplary embodiments are for illustrative purposes only, and it will be apparent to those of ordinary skill in the art that the scope of the present invention is not construed as being limited by these exemplary embodiments.

Example 1. Inhibition of Concentration Increase of Intracellular Calcium Ions by PAR2-AP in HT-29 Cells Punicalagin, which is a natural product of the present invention, was purchased from SIGMA-ALDRICH and used.

After colon cancer cells (HT-29) were cultured for 48 hours in a 96-well micro plate with the RPMI1640 culture medium, the culture medium was removed, and then, 100 μL of the Flou4-NW dye mixture was added. While blocking the light, it was stabilized for 1 hour such that a calcium ion dye ($Ca^{2+}$ dye) was loaded into the cells. Next, after treating punicalin (0, 3, 10, and 30 μM), punicalagin (0, 0.3, 1, 2, 3, and 10 μM), or ellagic acid (0, 30, and 100 μM) for 10 minutes by concentration, each well was treated with 30 μM PAR2-AP (PAR2-activating peptide, SLIGRL-$NH_2$) to measure the concentration change in intracellular calcium ions.

Figure 1:
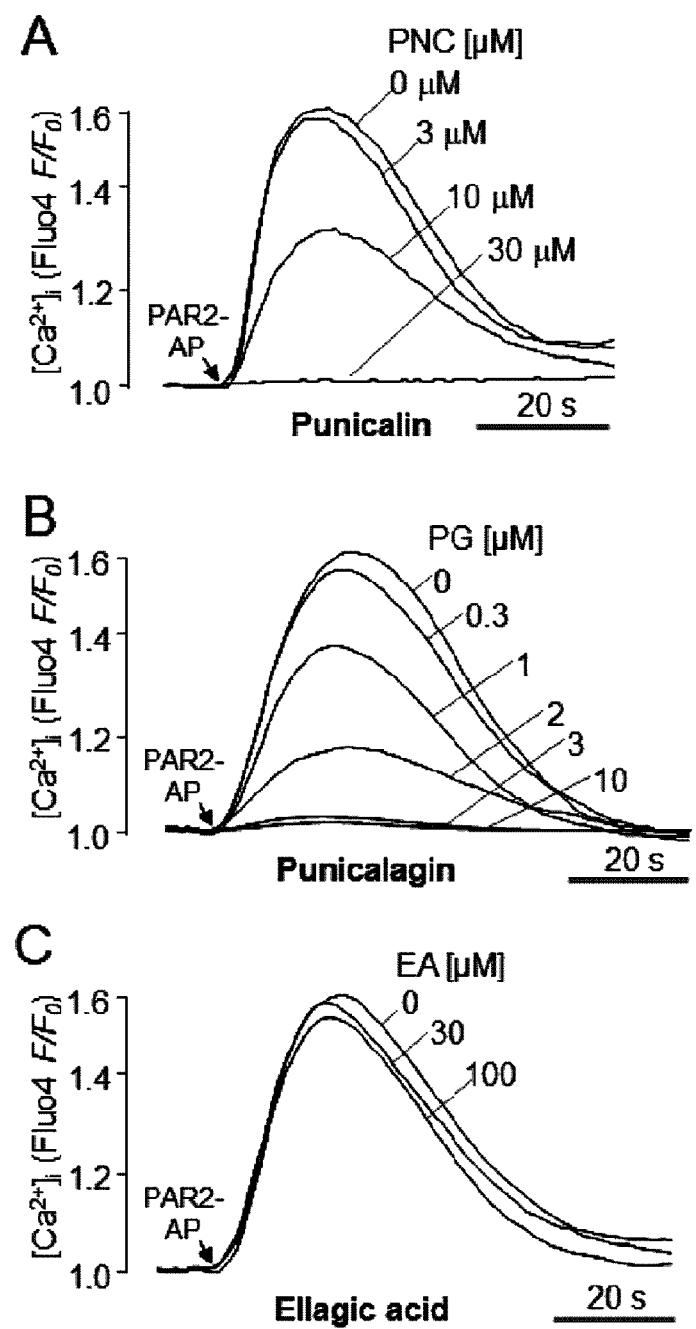
FIG. 1 is a result of confirming an effect in which punicalin (PNC), punicalagin (PG), or ellagic acid (EA) inhibited an increase in the concentration of intracellular calcium ions by PAR2-AP (activating peptide) in HT-29 cells according to an exemplary embodiment of the present invention.

As a result, as shown in FIG. 1, it was confirmed that punicalagin (PG) strongly inhibited the PAR2 receptor by about 10 times or more compared to punicalin (PNC), and $IC_{50}$ was 1.45 μM. Ellagic acid, which is abundant in pomegranate peel along with punicalagin and punicalin, did not inhibit the PAR2 receptor even at a high concentration (100 μM).

Example 2. Specific Inhibition of PAR2 Activity in HT-29 Cells

Figure 2:
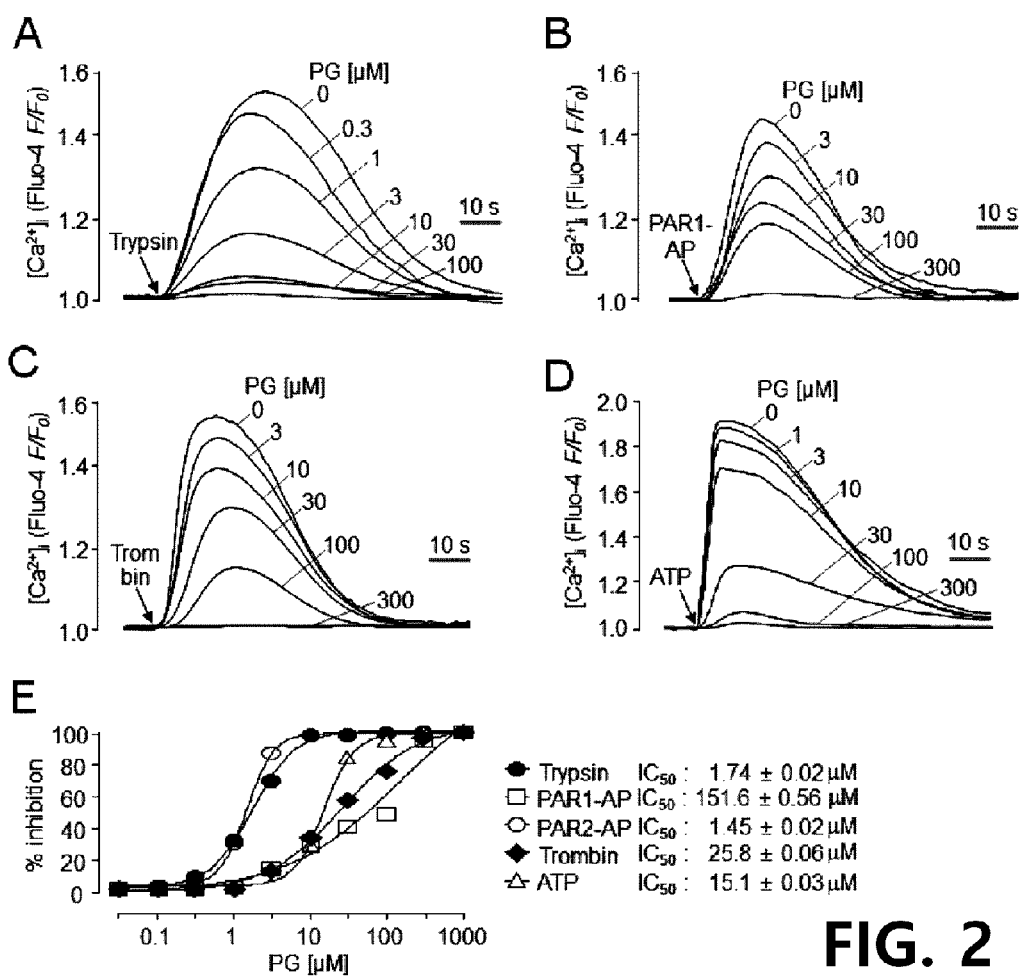
FIG. 2 is a result of confirming the specificity of punicalagin that inhibited the activity of PAR2 in HT-29 cells. Panels A to D of FIG. 2 are results of measuring the concentration changes in intracellular calcium ions when trypsin (panel A), PAR1-AP (panel B), thrombin (panel C), and ATP (panel D) were treated after treating punicalagin at each concentration; and panel E of FIG. 2 is a graph comparing the inhibitory effect of concentration increases of intracellular calcium ions by trypsin, PAR1-AP, PAR2-AP, thrombin, and ATP depending on the concentration of punicalagin.

After colon cancer cells (HT-29) were cultured for 48 hours in a 96-well micro plate with the RPMI1640 culture medium, the culture medium was removed, and then, 100 μL of the Flou4-NW dye mixture was added. While blocking the light, it was stabilized for 1 hour such that a calcium ion dye ($Ca^{2+}$ dye) was loaded into the cells. Next, punicalagin was pretreated by concentration (0, 0.3, 1, 3, 10, 30, and 100 μM) for 10 minutes, and by treating 100 nM trypsin, it was measured for about 70 seconds at 1-second intervals to determine whether the concentration changes of intracellular calcium ions by PAR2 activation were an inhibitory effect by punicalagin (panel A of FIG. 2). In the same manner as the above, after punicalagin was pretreated by concentration (0, 1, 3, 10, 30, 100, and 300 μM), by treating 100 μM PAR1-AP (panel B of FIG. 2), 10 unit/mL thrombin (panel C of FIG. 2), and 100 μM ATP (panel D of FIG. 2), the concentration changes in intracellular calcium ions were measured for 70 seconds at 1-second intervals in each case. As a result, it was confirmed that as the concentration of punicalagin increased, the effect of inhibiting an increase in the concentration of calcium ions was also improved.

In addition, it was compared how much it inhibited an increase in the concentration of intracellular calcium ions by trypsin, PAR1-AP, PAR2-AP, thrombin, and ATP depending on the concentration of punicalagin. As a result, as shown in panel E of FIG. 2, it was confirmed that punicalagin selectively inhibited the activity of PAR2 by about 10 times or more, compared to ATP, thrombin, and PAR1-AP.

Example 3. Inhibition of CaCC $Cl^-$ Current by PAR2 Activity in Human Conjunctival Cells After primary cultured human conjunctival epithelial cells expressing PAR2 were cultured in a transwell, followed by removal of a culture medium on the side of an apical membrane, retinoic acid was added to the side of a basolateral membrane to differentiate for about 2 weeks (*Invest Ophthalmol Vis Sci.* 2013 Oct. 29; 54(10): 7143-52), and then, short-circuit currents were measured using a Ussing chamber. After a regular $HCO_3^-$ solution (120 mM NaCl, 5 mM KCl, 1 mM $MgCl_2$, 2.5 mM HEPES, 1 mM $CaCl_2$, 10 mM glucose, and 25 mM $NaHCO_3$) was added in a luminal bath and basolateral bath of the Ussing chamber, it was stabilized for 20 minutes, and then, 100 µM amiloride was treated to inhibit the epithelial sodium channel (epithelial Na channel, ENaC) activity. Next, 100 µM PAR1-AP or 100 µM PAR2-AP was treated to measure the calcium-activated chloride channel (CaCC)-dependent $Cl^-$ secretion promoting effect through PAR1 and PAR2 receptor activations. Next, by treating 10 µM forskolin, which is a an activator of the cystic fibrosis transmembrane conductance regulator (CFTR), the effect of promoting $Cl^-$ secretion by the cystic fibrosis transmembrane conductance regulator (CFTR) channel was measured, and then, by treating 10 µM $CFTR_{ihn}$-172(5-[(4-carboxyphenyl)methylene]-2-thioxo-3-[(3-trifluoromethyl)phenyl-4-thiazolidinone]) (*J Clin Invest.* 2002 December; 110(11): 1651-8), which is a CFTR inhibitor, it was confirmed that $Cl^-$ secretion by the CFTR channel was inhibited (panel A of FIG. 3).

Meanwhile, $Cl^-$ secretion by PAR1-AP was not measured as a result of the above experiment, and in order to confirm the inhibitory effect of $Cl^-$ secretion during punicalagin treatment. ENaC was stabilized in the same manner as above, and then, it was treated with 100 µM amiloride to inhibit ENaC activity. Next, 10 µM punicalagin was treated for 10 minutes, and 100 µM PAR2-AP was treated. As a result, it was confirmed that when punicalagin was treated, it was confirmed that an increase in CaCC-dependent $Cl^-$ secretion was inhibited when the PAR2 receptor was activated by the PAR2-AP treatment (panel B of FIG. 3).

Example 4. Inhibitory Effect of Cytokine by PAR2-AP in Human Conjunctival Cells

In order to determine whether punicalagin inhibits cytokine secretion by PAR2 receptor activity, human conjunctival epithelial cells, which were primary cultured and differentiated in a transwell, were treated with 100 µM PAR2-AP or 10 µM punicalagin for 24 hours, and then, by collecting the culture medium from the apical membrane, cytokine concentrations were measured by the enzyme-linked immunosorbent assay.

Figure 4:
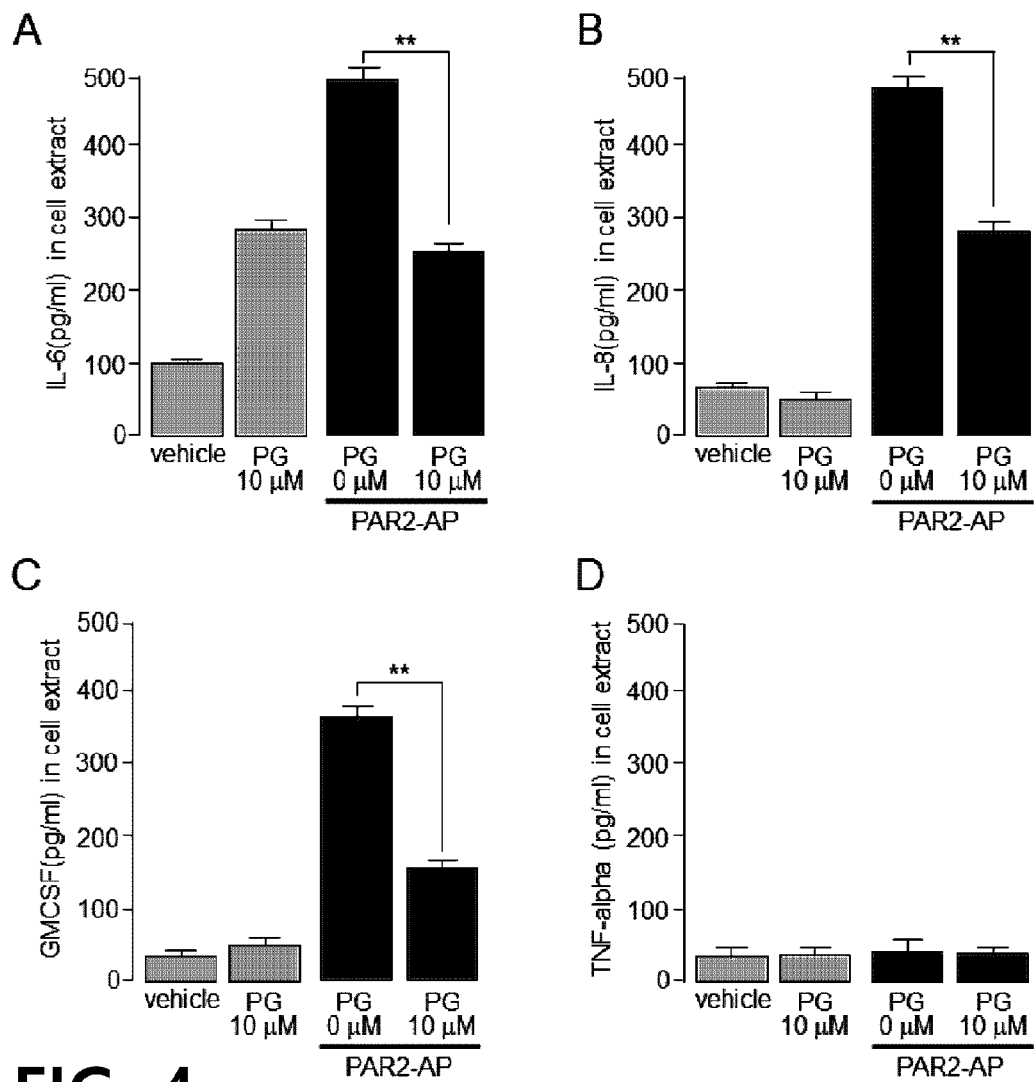
FIG. 4 is a result of confirming whether punicalagin inhibited cytokine secretion by PAR2-AP in primary cultured human conjunctival epithelial cells.

As a result, as shown in FIG. 4, it was confirmed that interleukin-6 (IL-6), interleukin-8 (IL-8), and the granulocyte-macrophage colony-stimulating factor (GMCSF), which were induced by the PAR2-AP treatment, were inhibited by punicalagin by 59.5% (panel A of FIG. 4), 61.6% (panel B of FIG. 4), and 66.8% (panel C of FIG. 4), respectively. Meanwhile, tumor necrosis factor alpha (TNF-α) was not increased by PAR2-AP (panel D of FIG. 4).

Example 5. Inhibitory Effect of Cytokine Secretion by House Dust Mite in Human Conjunctival Cells In order to determine whether punicalagin has an effect of inhibiting cytokine secretion by house dust mites (HDM), after removing a culture medium of conjunctival epithelial cells that were primary cultured and differentiated in a transwell, 300 µL of the Flou4-NW dye mixture was added, and then, it was stabilized for 1 hour such that a $Ca^{2+}$ dye was loaded into the cells while blocking the light. Next, punicalagin was pretreated by concentration (0, 10, and 30 µM) for 10 minutes, and then, it was treated with a 10 µg/mL house dust mite extract (HDM extract). Afterwards, the concentration change of calcium ions ($Ca^{2+}$) was measured for 3 minutes at 1-second intervals, and 100 µM PAR2-AP was treated to measure whether punicalagin inhibited the concentration change of intracellular calcium ions by PAR2 receptor activation.

As a result, when punicalagin was not treated, the concentration of intracellular calcium ions was increased by PAR2 receptor activation in primary cultured human conjunctival cells when they were treated with house dust mites and PAR2-AP (panel A of FIG. 5). However, when 10 µM punicalagin was treated, it was confirmed that the concentration increases of intracellular calcium ions by house dust mites and PAR2-AP were all inhibited by punicalagin (panel B of FIG. 5).

Next, conjunctival epithelial cells showing a high response to the concentration increase of intracellular calcium ions by HDM and PAR2-AP were treated with 1, 3, and 10 µM punicalagin, and after treating with 10 µg/mL HDM for 24 hours, secreted IL-6 cytokines were measured by enzyme immunoassay. As a result, it was confirmed that 1, 3, and 10 µM punicalagin inhibited about 50, 91, and 93% of IL-6 cytokines that were increased by HDM, respectively (panel C of FIG. 5).

Example 6. Alleviation Effect of Colitis Caused by DSS in Animal Experiments

In 7-week-old C57BL6N mice, it was confirmed whether punicalagin has an effect of alleviating symptoms of colitis induced by dextran sodium sulfate (DSS).

Specifically, while dextran sodium sulfate (DSS), which is a colitis-causing substance, was diluted in water at 2.5% and was fed to the mice for 9 days, 1 mg/kg (n=4), 3 mg/kg (n=4), or 10 mg/kg (n=5) punicalagin was dissolved in physiological saline and intraperitoneally injected once every 48 hours, and the mice were weighed once a day. As control groups, a group which was fed only with 2.5% DSS (n=4), a group which was not fed with DSS and was not injected with punicalagin (n=3), and a group which was not fed with DSS and was injected with punicalagin at 10 mg/kg (n=3) were established, and weight changes, tissue damage, proinflammatory cytokine concentrations, and the like were measured.

As a result, mice, in which colitis was not induced, did not lose weight and no bloody stool was observed, but mice, in which colitis was induced by DSS, developed bloody stool and rapid weight loss. Meanwhile, it was confirmed that when 1 mg/kg, 3 mg/kg, or 10 mg/kg punicalagin was administered, punicalagin inhibited weight loss by DSS in a concentration-dependent manner (panels A to B of FIG. 6).

In addition, as a result of measuring the length by extracting the colon tissue of the mice that were used in the above experiment in order to confirm whether punicalagin could inhibit a decrease in the length of the colon due to inflammation of the colon, it was observed that the length of the colon which was reduced by DSS recovered by punicalagin (panel C of FIG. 6). It was confirmed that punicalagin inhibited colon tissue damage caused by DSS (panel D of FIG. 6) and significantly reduced the concentration of proinflammatory cytokines that were increased by DSS (panel E of FIG. 6).

Example 7. Alleviation Effect of Colitis Caused by TNBS in Animal Experiments

In 7-week-old SD rats, it was confirmed whether punicalagin had an effect of alleviating the symptoms of colitis induced by trinitrobenzene sulfonic acid (TNBS).

Specifically, 80 mg/kg TNBS was diluted in 50% ethanol and injected into the anus of rats, and punicalagin (1, 3, and 10 mg/kg) was intraperitoneally injected for 3 days. As control groups, a group which was intraperitoneally injected with PBS and treated with 50% ethanol only (n=3) and a group which was intraperitoneally injected with PBS and was treated only with TNBS (n=3) were established, and weight change was measured. After 3 days, the rats of each group were sacrificed, the colon was extracted to measure the length, and the spleen was extracted and weighed.

As a result, punicalagin significantly inhibited weight loss, colon length reduction, and a weight increase of the spleen by TNBS in a concentration-dependent manner (panels A to C of FIG. 7). In addition, it was confirmed that punicalagin inhibited colon tissue damage caused by TNBS in a concentration-dependent manner (panel D of FIG. 7), and significantly decreased all of the concentrations of inflammatory cytokines (INF-γ, IL-2, IL-4, IL-6, IL-β, TNF-α, IL-1β, etc.) that were increased by TNBS (panels E to N of FIG. 7).

Example 8. Alleviation Effect of Acute Pancreatitis Caused by Caerulean

In 6-week-old SD rats, it was confirmed whether punicalagin has an effect of alleviating symptoms of acute pancreatitis induced by caerulein.

Specifically, the rats were treated with 10 mg/kg punicalagin, and after 30 minutes, 40 μg/kg of caerulein, which is an acute pancreatitis-inducing substance, was intraperitoneally injected, and then, after 2 hours, the pancreas of the experimental animals was extracted and analyzed.

First, the weight of the extracted pancreas was measured to determine whether punicalagin inhibits edema, which is a symptom of acute pancreatitis. As a result, it was confirmed that when 10 mg/kg punicalagin was administered to mice, in which acute pancreatitis was induced by caerulein, the edema of the pancreas was inhibited by 95% or more (panel A of FIG. 8). However, in a group treated with 10 mg/kg ellagic acid (EA), which is a metabolite of punicalagin and one of the main components of pomegranate peel, edema caused by caerulein was not significantly inhibited.

Next, as a result of observing the nucleus and cytoplasm of the extracted pancreatic tissue with a microscope through H&E staining in order to confirm the damage to pancreatic cells by caerulein, it was confirmed that in the rats administered with caerulein, the distance between pancreatic cells was increased and the cells were damaged due to symptoms of acute pancreatitis. However, in the case of a group which was pretreated with punicalagin at 3 mg/kg and treated with caerulein, it showed a result that the edema of the pancreas and cell damage were strongly inhibited (panel B of FIG. 8). In addition, it was confirmed that punicalagin significantly decreased all of the concentrations of inflammatory cytokines (INF-γ, IL-2, IL-4, IL-6, IL-β, TNF-α, IL-1β, etc.) that were increased by caerulein (panels C to K of FIG. 8).

Example 9. Alleviation Effect of Nephritis in Animal Experiments

With NZB/W F1 mice that were purchased from Central Lab. Animal Inc., the effect of punicalagin on symptoms of lupus nephritis was confirmed.

In 23-week-old mice in which proteinuria began to increase due to lupus nephritis, 3 mg/kg, 1 mg/kg, and 0.3 mg/kg punicalagin (PG) were dissolved in physiological saline and were intraperitoneally injected three times a week, and proteinuria was measured twice a week. As control groups, there were two groups including a nephritis-induced group that was injected only with physiological saline and a nephritis-induced group that was injected with 7 mg/kg methylprednisolone (MPL), which is a standard therapeutic agent for lupus nephritis, and proteinuria was measured twice a week (panel A of FIG. 9).

As a result, mortality from 23 weeks to 30 weeks was observed only in the nephritis-induced group, and none of the subjects died in the groups that were treated with punicalagin (panel B of FIG. 9). In addition, high proteinuria was observed in the nephritis-induced group, whereas the groups that were treated with 3 mg/kg and 1 mg/kg punicalagin showed 60% lower proteinuria compared to the nephritis-induced group, and proteinuria was low at a level treated with 7 mg/kg methylprednisolone (MPL) (panel C of FIG. 9). Serum creatinine concentrations were also lower in the punicalagin-treated groups than in the nephritis-induced group, and it showed the lowest serum creatinine concentration in the 3 mg/kg punicalagin-treated group (panel D of FIG. 9).

Example 10. Protective Effect of Kidney Structure in Animal Experiments

Next, the protective effect of punicalagin on renal structural damage against lupus nephritis was histologically evaluated. To this end, kidneys were extracted and PAS stained in 30-week-old mice, and the degree of damage to glomeruli, ducts, and blood vessels was histologically quantified. In addition, when lupus nephritis was induced, the expressions of IgG and C3, which are autoantibodies mostly expressed in kidney tissues, were fluorescence-stained and observed under a fluorescence microscope.

As a result, the degree of damage to all of glomeruli, ducts, and blood vessels was alleviated in mice treated with 3 mg/kg, 1 mg/kg, and 0.1 mg/kg punicalagin (PG) compared to nephritis-induced mice that were treated with physiological saline only, and it was similar to a level treated with methylprednisolone (MPL) which is a standard therapeutic agent (panels A to B of FIG. 10). In addition, as a result of fluorescence microscopy observation, compared to the large amount of IgG and C3 depositions in the nephritis-induced mice that were treated with physiological saline only. IgG and C3 depositions were significantly reduced in the mice treated with 3 mg/kg, 1 mg/kg, and 0.3 mg/kg punicalagin, and particularly in the group treated with 3 mg/kg and 1 mg/kg punicalagin, it was similar to a level treated with methylprednisolone (panels C to D of FIG. 10).

Example 11. T Cell Changes by Punicalagin

In order to determine the mechanism of the alleviating effect of punicalagin on lupus nephritis, the spleen was extracted from 30-week-old mice, the spleen weight and the number of splenocytes were measured, and changes in T cells in the spleen were analyzed by FACS.

As a result, compared to nephritis-induced mice treated with physiological saline only, the weight of the spleen was not increased by the immune response in mice that were treated with 3 mg/kg, 1 mg/kg, and 0.3 mg/kg punicalagin, which was similar to the group treated with methylprednisolone, and the total number of splenocytes was not increased (panels A to C of FIG. 11).

In addition, as a result of measuring the number of CD4 T cells in the spleen and the expressions of TH1, TH2, and TH17 T cells, all of these were significantly reduced in the mice treated with 3 mg/kg and 1 mg/kg punicalagin, compared to the nephritis-induced mice that were treated with physiological saline only, and the expression of regulatory T cells (Treg) was significantly increased in the mice treated with 3 mg/kg punicalagin (panels D to H of FIG. 11).

Example 12. Serum Cytokine Changes by Punicalagin

After serum was isolated from 30-week-old mice, it was analyzed by the enzyme immunoassay to determine whether punicalagin inhibited or increased cytokines that were expressed by lupus nephritis.

As a result, the expressions of IFN-γ, IL-17A, and IL-6, which are inflammatory cytokines, were increased in the nephritis-induced mouse group treated only with physiological saline, whereas all of the expressions were reduced in the mice treated with 3 mg/kg, 1 mg/kg, and 0.3 mg/kg punicalagin, and these were low, which was similar to the expression level of the group treated with methylprednisolone, which is a standard therapeutic agent (panels A to C of FIG. 12).

In addition, in the case of the expressions of IL-10 and TGF-β1, which are inflammatory cytokines, these were increased in all groups treated with 3 mg/kg, 1 mg/kg, and 0.3 mg/kg punicalagin (panels D to E of FIG. 12).

Example 13. Reduction Effect of B Cell Antibodies by Punicalagin

In order to determine the alleviating effect of punicalagin on lupus nephritis, serum was isolated from 30-week-old mice, and the expression of B cell autoantibodies was analyzed by the enzyme immunoassay.

As a result, compared to the group of nephritis-induced mice treated with physiological saline only, all of the expressions of anti-dsDNA, IgG1, IgG2a, IgG2b, and IgG3 were decreased in the serum of mice treated with 1 mg/kg and 10 mg/kg punicalagin. In particular, it was significantly reduced in the group treated with 1 mg/kg punicalagin (panels A to E of FIG. 13).

In addition, kidney weight was increased in the nephritis-induced mice treated only with physiological saline by the inflammatory response, whereas kidney weight was reduced in the mice treated with 1 mg/kg punicalagin (panel F of FIG. 13).

Example 14. Expression Changes of VCAM-1 and ICAM-1 by Punicalagin

In order to determine the alleviation mechanism of punicalagin against lupus nephritis, the expressions of VCAM-1 and ICAM-1 were analyzed by immunohistochemical staining in renal tissues of 30-week-old mice.

As a result, compared to the nephritis-induced mouse group treated with physiological saline only, the expressions of VCAM-1 and ICAM-1 were significantly reduced in all of the kidney tissues of the mice treated with 3 mg/kg, 1 mg/kg, and 0.3 mg/kg punicalagin (panels A to B of FIG. 14).

Example 15. Effect of Punicalagin on Cell and Animal Tissues

In order to determine the toxicity of punicalagin, the effect of NIH3T3 cells on cell viability and the weight change of 8-week-old wild-type mice were evaluated, and the heart, liver, and lung were extracted from 30-week-old lupus mice and were histologically evaluated by performing hematoxylin-eosin staining.

As a result, punicalagin had no effect on the viability of NIH3T3 cells (panel A of FIG. 15) up to 30 μM, and there was no weight change in wild-type mice that were intraperitoneally injected with 10 mg/kg punicalagin at 2-day intervals (panel B of FIG. 15). Also, no histological difference was observed in the heart, liver, and lung tissues of lupus mice treated with 3 mg/kg, 1 mg/kg, and 0.3 mg/kg punicalagin, compared to the nephritis-induced group treated with physiological saline only, or the group treated with methylprednisolone, which is a standard therapeutic agent (panel C of FIG. 15).

Example 16. Effect of Punicalagin on Activity of Glomerular Podocytes

The effects of punicalagin on cellular signal changes and inflammatory cytokine secretion by PAR2 receptor activity in human glomerular podocytes were evaluated.

As a result, punicalagin inhibited phosphorylation of ERK 1/2 according to PAR2 receptor activity by PAR2-AP in a concentration-dependent manner (panel A of FIG. 16), and also inhibited phosphorylation of NF-κB P65 according to PAR2 receptor activity in a concentration-dependent manner (panel B of FIG. 16). The expression amounts of VCAM-1 and ICAM-1, which induce the influx of inflammatory cells in lupus nephritis, were increased by the PAR2 receptor activity, and the expression amounts of VCAM-1 (panel C of FIG. 16) and ICAM-1 (panel D of FIG. 16) were significantly reduced by punicalagin. Activation of the PAR2 receptor significantly increased the expressions of inflammatory cytokines (IL-6, IFN-γ, TNF-α, and IL-8) in glomerular podocytes, and the expressions of these inflammatory cytokines were significantly reduced by punicalagin in a concentration-dependent manner (panels E to H of FIG. 16).

Example 17. Inhibition of Concentration Increase of Calcium Ions by PAR2 Inhibition in HaCaT Cells After keratinocytes (HaCaT) were cultured for 48 hours in a 96-well micro plate with the DMEM culture medium, the culture medium was removed, and then, 100 μL of the Flou4-NW dye mixture was added. While blocking the light, it was stabilized for 1 hour such that a calcium ion dye ($Ca^{2+}$ dye) was loaded into the cells. 100 μM punicalagin was treated, and the concentration change of intracellular calcium ions was measured for 5 minutes (panel A of FIG. 17). Next, punicalin (0, 1, 3, 10, 20, 30, 100, and 300 μM) by concentration (panel B of FIG. 17) or punicalagin (0, 1, 3, 5, 10, 20, 30, and 100 μM) by concentration (panel C of FIG. 17) was treated for 10 minutes, and then, each well was treated with 0.1 μM trypsin to measure the concentration change of intracellular calcium ions according to PAR2 receptor activation.

As a result, as shown in FIG. 17A, 100 μM punicalagin (PG) had no effect on the concentration of intracellular calcium ions in keratinocytes. In addition, both punicalin (PNC) and punicalagin inhibited PAR2 receptor activity by trypsin in a concentration-dependent manner (panels B to C of FIG. 17). In addition, as shown in panel D of FIG. 17, it was confirmed that punicalagin strongly inhibited the PAR2 receptor by about 3.7 times or more compared to punicalin, and $IC_{50}$ was 5.24 μM.

Example 18. Alleviation Effect of Pruritis by PAR2 Receptor in Animal Experiments In seven-week-old C57BL6N mice, it was confirmed whether punicalagin (PG) has an effect of alleviating pruritus symptoms induced by PAR2 receptor activation by PAR2-AP (activating peptide). In addition, the effects of punicalin (PNC) and ellagic acid (EA), which are metabolites of punicalagin and contained in pomegranate peel in a large amount, were also confirmed.

Specifically, each of 0, 1, 3, and 10 mg/kg punicalagin (n=4) was dissolved in physiological saline and intraperitoneally injected, and after 30 minutes, 100 μg of PAR2-AP was intradermally injected to induce pruritus. As control groups, a group which was intraperitoneally injected with physiological saline only (n=4) and a group which was intraperitoneally injected with 10 mg/kg punicalagin (n=4) were established, and the number of scratches was measured for 40 minutes.

As a result, as shown in panel A of FIG. 18, the group which was intraperitoneally injected with physiological saline and intradermally injected with PAR2-AP showed that the number of scratches was 104 times during the initial 10 minutes, whereas the numbers of scratches were suppressed to about 59, 28, 14 times in the groups in which pruritus was induced by PAR2-AP after punicalagin (1, 3, and 10 mg/kg) was injected. In addition, as shown in panel B of FIG. 18, when the number of times that the mice scratched by PAR2-AP was measured for 40 minutes, the group injected with PAR2-AP showed that the number of scratches was about 240 times, but the groups injected with punicalagin (1, 3, and 10 mg/kg) showed that the numbers of scratches were suppressed to about 188, 103, and 40 times. However, the group which was pretreated with punicalin (10 mg/kg) that weakly inhibits the PAR2 receptor (n=3) showed that the number of scratches was weakly reduced to about 197 times. In addition, even at high concentrations, the numbers of scratches were not significantly reduced for the group injected with ellagic acid (3 mg/kg) that does not inhibit PAR2 receptor activity (n=3).

Example 19. Alleviation Effect or Pruritus by DNFB in Animal Experiments

In 12-week-old ICR mice, it was confirmed whether punicalagin inhibits pruritus caused by atopic dermatitis induced by 1-fluoro-2,4-dinitrobenzene (DNFB).

Specifically, as shown in panel A of FIG. 19, punicalagin (PG) was dissolved in physiological saline and intraperitoneally injected at 3 mg/kg daily for 17 days, and atopic dermatitis and pruritus were induced by treating 0.15% DNFB dissolved in acetone with a cotton swab on the back of the mice on the 10th, 13th, 20th, and 27th days. The inflammation of the skin was observed in a group which was intraperitoneally injected with physiological saline and treated with acetone (n=8), a group which was intraperitoneally injected with physiological saline and treated with DNFB (n=8), or a group which was intraperitoneally injected with punicalagin and treated with DNFB, and the number of scratches was measured for 30 minutes.

As a result, atopic dermatitis was significantly reduced in the group treated with punicalagin (panels A to C of FIG. 19). In addition, the number of scratches by the mice induced with atopic dermatitis by DNFB was significantly reduced by punicalagin, and when the number of scratches was measured for 30 minutes, punicalagin suppressed about 60% of the number of scratches caused by DNFB (panels D to E of FIG. 19).

The invention claimed is:

1. A method for inhibiting protease-activated receptor 2 (PAR2) activity, comprising administering punicalagin, a stereoisomer thereof, or a pharmaceutically acceptable salt thereof to a subject in need thereof.

2. The method of claim 1, wherein the punicalagin, a stereoisomer thereof, or a pharmaceutically acceptable salt thereof
   a) inhibits an increase in intracellular calcium ions ($Ca^{2+}$) by PAR2 activity;
   b) inhibits activation of ERK1/2 and NF-κB by PAR2 activity;
   c) inhibits increased secretion of chloride ions ($Cl^-$) by PAR2 activity; or
   d) inhibits secretion of a cytokine.

3. The method of claim 2, wherein the cytokine is one or more selected from the group consisting of interferon-gamma (IFN-γ), interleukin-β (IL-1β), interleukin-2 (IL-2), interleukin-4 (IL-4), interleukin-6 (IL-6), interleukin-8 (IL-8), interleukin-10 (IL-10), interleukin-17A (IL-17A), granulocyte-macrophage colony-stimulating factor (GMCSF), and tumor necrosis factor alpha (TNF-α).

* * * * *